US012698291B2

(12) United States Patent
Smrcina et al.

(10) Patent No.: US 12,698,291 B2

(45) Date of Patent: Aug. 4, 2026

(54) PIKfyve KINASE INHIBITORS

(71) Applicant: AcuraStem Incorporated, Pasadena, CA (US)

(72) Inventors: Martin Smrcina, Oro Valley, AZ (US); Ronghua Li, Oro Valley, AZ (US); Anil Nair, Oro Valley, AZ (US); Paul August, Oro Valley, AZ (US); Kirsten Bjergarde, Oro Valley, AZ (US)

(73) Assignee: ACURASTEM INCORPORATED, Pasadena, CA (US)

( * ) Notice: Subject to any disclaimer, the term of this patent is extended or adjusted under 35 U.S.C. 154(b) by 0 days.

(21) Appl. No.: 18/612,147

(22) Filed: Mar. 21, 2024

(65) Prior Publication Data

US 2024/0352026 A1 Oct. 24, 2024

Related U.S. Application Data

(63) Continuation of application No. 16/641,159, filed as application No. PCT/US2018/048369 on Aug. 28, 2018, now abandoned.

(60) Provisional application No. 62/551,047, filed on Aug. 28, 2017.

(51) Int. Cl.

*C07D 491/048* (2006.01)
*C07D 405/14* (2006.01)
*C07D 413/14* (2006.01)

(52) U.S. Cl.

CPC ....... *C07D 491/048* (2013.01); *C07D 405/14* (2013.01); *C07D 413/14* (2013.01)

(58) Field of Classification Search

CPC ......................... C07D 491/048; C07D 405/14; C07D 413/14; C07D 417/14

See application file for complete search history.

(56) References Cited

U.S. PATENT DOCUMENTS

| | | | | |
|---|---|---|---|---|
| 2,309,663 | A | 2/1943 | Oldham et al. | |
| 3,687,808 | A | 8/1972 | Thomas, Jr. et al. | |
| 6,268,490 | B1 | 7/2001 | Imanishi et al. | |
| 6,525,191 | B1 | 2/2003 | Ramasamy | |
| 6,660,733 | B2 | 12/2003 | Sun et al. | |
| 6,670,461 | B1 | 12/2003 | Wengel et al. | |
| 6,770,748 | B2 | 8/2004 | Imanishi et al. | |
| 6,794,499 | B2 | 9/2004 | Wengel et al. | |
| 6,858,606 | B2 | 2/2005 | Sun et al. | |
| 7,034,133 | B2 | 4/2006 | Wengel et al. | |
| 7,053,207 | B2 | 5/2006 | Wengel | |
| 7,547,684 | B2 | 6/2009 | Seth et al. | |
| 7,572,582 | B2 | 8/2009 | Wengel et al. | |
| 7,666,854 | B2 | 2/2010 | Seth et al. | |
| 7,750,131 | B2 | 7/2010 | Seth et al. | |
| 8,030,467 | B2 | 10/2011 | Seth et al. | |
| 8,034,909 | B2 | 10/2011 | Wengel et al. | |
| 8,080,644 | B2 | 12/2011 | Wengel et al. | |
| 8,088,746 | B2 | 1/2012 | Seth et al. | |
| 8,153,365 | B2 | 4/2012 | Wengel et al. | |
| 8,236,795 | B2 * | 8/2012 | Sun | C07D 417/14 514/235.8 |
| 8,268,980 | B2 | 9/2012 | Seth et al. | |
| 8,501,805 | B2 | 8/2013 | Seth et al. | |
| 8,530,640 | B2 | 9/2013 | Seth et al. | |
| 8,546,556 | B2 | 10/2013 | Seth et al. | |
| RE44,779 | E | 2/2014 | Imanishi et al. | |
| 9,012,421 | B2 | 4/2015 | Migawa et al. | |
| 9,234,885 | B2 | 1/2016 | Chandran et al. | |
| 10,729,694 | B2 | 8/2020 | Lichenstein et al. | |
| 12,104,159 | B2 | 10/2024 | Chang et al. | |
| 2003/0104410 | A1 | 6/2003 | Mittmann | |
| 2005/0026164 | A1 | 2/2005 | Zhou | |
| 2005/0038023 | A1 * | 2/2005 | Bebbington | C07D 407/14 544/122 |
| 2006/0024715 | A1 | 2/2006 | Liu et al. | |
| 2006/0199804 | A1 | 9/2006 | Hummersone et al. | |
| 2008/0039618 | A1 | 2/2008 | Allerson et al. | |
| 2012/0009151 | A1 | 1/2012 | Han et al. | |
| 2013/0273070 | A1 | 10/2013 | Purcell Ngambo | |
| 2015/0065519 | A1 | 3/2015 | Chakravarty et al. | |

(Continued)

FOREIGN PATENT DOCUMENTS

| | | | | |
|---|---|---|---|---|
| DE | 4031798 | A1 * | 4/1992 | A01N 43/54 |
| EP | 3676264 | A1 | 7/2020 | |

(Continued)

OTHER PUBLICATIONS

CAS Registry No. 1467559-07-4, which entered STN on Nov. 1, 2013 (Year: 2013).*

CAS Registry No. 1500340-86-2, which entered STN on Dec. 22, 2013 (Year: 2013).*

CAS Registry No. 1499689-68-7, which entered STN on Dec. 20, 2013 (Year: 2013).*

CAS Registry No. 1978735-76-0, which entered STN on Aug. 24, 2016 (Year: 2016).*

International Search Report and Written Opinion for International Application No. PCT/US2018/048369, European Patent Office, Netherlands, mailed on Feb. 11, 2019, 23 pages.

CAS Registry No. 696636-91-6, which entered STN on Jun. 21, 2004 (Year: 2004).

CAS Registry No. 1501782-42-8, which entered STN on Dec. 23, 2013 (Year: 2013).

(Continued)

*Primary Examiner* — Matthew P Coughlin

(74) *Attorney, Agent, or Firm* — Sterne, Kessler, Goldstein & Fox P.L.L.C.

(57) ABSTRACT

The present invention relates to compounds of formula (I) (shown below) useful as inhibitors of phosphatidylinositol-3-phosphate 5-kinase (PIKfyve) as well as their use for treating diseases and disorders associated with PIKfyve.

(I)

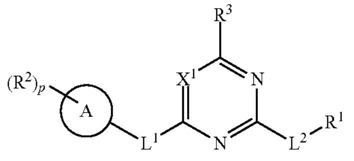

18 Claims, No Drawings

(56) References Cited

U.S. PATENT DOCUMENTS

| | | | |
|---|---|---|---|
| 2015/0191727 | A1 | 7/2015 | Migawa et al. |
| 2018/0161335 | A1 | 6/2018 | Ichida et al. |
| 2020/0199136 | A1 | 6/2020 | Smrcina et al. |
| 2021/0009718 | A1 | 1/2021 | Ambrogelly et al. |
| 2021/0338683 | A1 | 11/2021 | Ichida et al. |
| 2022/0193204 | A1 | 6/2022 | Cruz et al. |
| 2023/0135152 | A1 | 5/2023 | Smrcina et al. |
| 2024/0197747 | A1 | 6/2024 | Ichida et al. |

FOREIGN PATENT DOCUMENTS

| | | | | |
|---|---|---|---|---|
| EP | 3753937 | A1 | 12/2020 | |
| EP | 3960875 | A1 | 3/2022 | |
| EP | 3967694 | A1 | 3/2022 | |
| EP | 4103281 | A1 | 12/2022 | |
| WO | WO-9914226 | A2 | 3/1999 | |
| WO | WO-0250065 | A2 | 6/2002 | |
| WO | WO-03101989 | A1 | 12/2003 | |
| WO | WO-2004106356 | A1 | 12/2004 | |
| WO | WO-2005007648 | A2 | 1/2005 | |
| WO | WO-2006128129 | A2 | 11/2006 | |
| WO | WO-2007134181 | A2 | 11/2007 | |
| WO | WO-2008067871 | A1 | 6/2008 | |
| WO | WO-2008125839 | A2 | 10/2008 | |
| WO | WO-2009016410 | A2 * | 2/2009 | ........... C07D 401/14 |
| WO | WO-2009083553 | A1 * | 7/2009 | ........... C07D 401/12 |
| WO | WO-2009150462 | A1 | 12/2009 | |
| WO | WO-2010149459 | A1 | 12/2010 | |
| WO | WO-2012101654 | A2 | 8/2012 | |
| WO | WO-2013014074 | A1 | 1/2013 | |
| WO | WO-2013052395 | A1 | 4/2013 | |
| WO | WO-2014016849 | A2 | 1/2014 | |
| WO | WO-2016210372 | A2 | 12/2016 | |
| WO | WO-2017012576 | A1 | 1/2017 | |
| WO | WO-2017015555 | A1 | 1/2017 | |
| WO | WO-2017070189 | A1 | 4/2017 | |
| WO | WO-2018137573 | A1 | 8/2018 | |
| WO | WO-2018137607 | A1 | 8/2018 | |
| WO | WO-2019046316 | A1 | 3/2019 | |
| WO | WO-2019222173 | A1 | 11/2019 | |
| WO | WO-2021154687 | A1 | 8/2021 | |
| WO | WO-2021155067 | A1 | 8/2021 | |
| WO | WO-2021163727 | A1 | 8/2021 | |
| WO | WO-2022271836 | A2 | 12/2022 | |
| WO | WO-2023215133 | A1 | 11/2023 | |
| WO | WO-2024167945 | A1 | 8/2024 | |

OTHER PUBLICATIONS

Baird, A.M., et al., "IL-23R is Epigenetically Regulated and Modulated by Chemotherapy in Non-Small Cell Lung Cancer," Front Oncol 3:162, Frontiers Media, Switzerland (Jun. 2013).

Cai, X., et al., "PIKfyve, a class Iii Pi kinase, is the target of the small molecular IL-12/IL-23 inhibitor apilimod and a player in Toll-like receptor signaling," Chem Biol 20(7):912-921, Cell Press, United States (Jul. 2013).

Wada, Y., et al., "Selective abrogation of Th1 response by STA-5326, a potent IL-12/IL-23 inhibitor," Blood 109(3):1156-1164, American Society of Hematology, United States (Feb. 2007).

Adamson, C.S., et al., "Antiviral Drug Discovery: Preparing for the Next Pandemic," Chemical Society Reviews 50(6):3647-3655, Chemical Society, United Kingdom (Mar. 2021).

Albaek, N., et al., "Analogues of a Locked Nucleic Acid with Three-Carbon 2,4-Linkages: Synthesis by Ring-Closing Metathesis and Influence on Nucleic Acid Duplex Stability and Structure," The Journal of Organic Chemistry 71(20):7731-7740, American Chemical Society, United States (Sep. 2006).

Shetty, R., et al., "Therapeutic opportunities to manage COVID-19/SARS-CoV-2 infection: Present and future," Indian Journal of Ophthalmology 68(5):693-702, Medknow Publications, India (Mar. 2020).

Balfour, H., "Nafamostat Inhibits SARS-CoV-2 Infection, Preventing COVID-19 Transmission," Drug Target Review, Mar. 2020, accessed at https://www.drugtargetreview.com/news/58915/nafamostat-inhibits-sars-cov-2-infection-preventing-covid-19-transmission/, 4 pages.

Yamaya, M., et al., "Protease Inhibitors: Candidate Drugs to Inhibit Severe Acute Respiratory Syndrome Coronavirus 2 Replication," The Tohoku Journal of Experimental Medicine 251(1):27-30, Tohoku University Medical Library, Japan (May 2020).

Barciszewski, J., et al., "Chapter 10: Locked Nucleic Acid Aptamers," Methods in Molecular Biology 535:165-186, Humana Press, United States (2009).

Yamamoto, M., et al., "The Anticoagulant Nafamostat Potently Inhibits SARS-CoV-2 Infection in Vitro: an Existing Drug With Multiple Possible Therapeutic Effects," BioRxiv 2020.04.22. 054981, pp. 1-19, Cold Spring Laboratory Press, United Kingdom (Apr. 2020).

Co-pending U.S. Appl. No. 18/818,329, inventors Chang, W.-H., et al., filed on Aug. 28, 2024, 68 pages (Not yet Published).

Co-pending U.S. Appl. No. 18/862,354, inventor Bjergarde, K., filed on Nov. 1, 2024, 53 pages (Not yet Published).

Wils, H., et al., "TDP-43 Transgenic Mice Develop Spastic Paralysis and Neuronal Inclusions Characteristic of Als and Frontotemporal Lobar Degeneration," Proceedings of the National Academy of Sciences of the United States of America 107(8):3858-3863, National Academy of Sciences, United States (Feb. 2010).

Cuesta-Geijo, M.A., et al., "Endosomal Maturation, Rab7 GTPase and Phosphoinositides in African Swine Fever Virus Entry," PLoS One 7(11):e48853, 13 Pages, Public Library of Science, United States (Nov. 2012).

Cuesta-Geijo, M.A., et al., "Redistribution of Endosomal Membranes to the African Swine Fever Virus Replication Site," Viruses 9(6):133, MDPI, Switzerland (Jun. 2017).

Englisch, U., and Gauss, D.H., "Chemically Modified Oligonucleotides as Probes and Inhibitors," Angewandte Chemie International Edition in English 30(6):613-629, Wiley-VCH, Germany (Jun. 1991).

EurekAlert, "Nafamostat is Expected to Prevent the Transmission of New Coronavirus Infection (COVID-19)," The Institute of Medical Science, The University of Tokyo, News Release, Mar. 2020, accessed at https://www.eurekalert.org/news-releases/838150, 4 Pages.

Freier, S.M., and Altmann, K.H., "The Ups and Downs of Nucleic Acid Duplex Stability: Structure-stability Studies on Chemically-modified DNA: RNA Duplexes," Nucleic Acids Research 25(22):4429-4443, Oxford University Press, United Kingdom (Nov. 1997).

Godwin, P., et al., "Targeting Nuclear Factor-kappa B to Overcome Resistance to Chemotherapy," Frontiers in Oncology 3:120, 10 Pages, Frontiers Media S.A., Switzerland (May 2013).

Hagedorn, P.H., et al., "Acute Neurotoxicity of Antisense Oligonucleotides After Intracerebroventricular Injection Into Mouse Brain Can Be Predicted from Sequence Features," Nucleic Acid Therapeutics 32(3):151-162, Mary Ann Liebert, Inc., United States (Jun. 2022).

Higuchi, T., and Stella, V., "Pro-drugs as Novel Delivery Systems," vol. 14 of the A.C.S. Symposium Series, and in Bioreversible Carriers in Drug Design, Roche, E.B., ed., American Pharmaceutical Association and Pergamon Press (1987).

Hoffmann, M., et al., "SARS-CoV-2 Cell Entry Depends on ACE2 and TMPRSS2 and Is Blocked by a Clinically Proven Protease Inhibitor," Cell 181(2):271-280, Cell Press, United States (Apr. 2020).

Wikipedia, "Coronavirus," Wikipedia.org, 2023, accessed at https://en.wikipedia.org/wiki/Coronavirus, 33 Pages.

Taylor, M., and Gerriets, V., "Acyclovir," NCBI Bookshelf, StatPearls Publishing, United States (May 2023), accessed at https://www.ncbi.nlm.nih.gov/books/NBK542180/, 8 Pages.

International Search Report and Written Opinion for Application No. PCT/US2021/070144, European Patent Office, Netherlands, mailed on May 10, 2021, 18 pages.

International Search Report and Written Opinion for Application No. PCT/US2022/034539, European Patent Office, Netherlands, mailed on Dec. 21, 2022, 20 pages.

International Search Report and Written Opinion for Application No. PCT/US2023/019770, European Patent Office, Netherlands, mailed on Jul. 20, 2023, 13 pages.

(56) References Cited

OTHER PUBLICATIONS

International Search Report and Written Opinion for Application No. PCT/US2024/014647, European Patent Office, Netherlands, mailed on Jul. 19, 2024, 16 pages.
Weir, M., et al., "Canine Coronavirus Disease," Coronavirus Disease in Dogs, (2021), accessed at https://vcahospitals.com/know-your-pet/coronavirus-disease-in-dogs, 2 Pages.
Kang, Y-L., et al., "Inhibition of PIKfyve kinase prevents infection by Zaire ebolavirus and SARS-CoV-2," PNAS 117(34):20803-20813, National Academy of Sciences (Aug. 2020).
Kausar, S., et al., "A Review: Mechanism of Action of Antiviral Drugs," International Journal of Immunopathology and Pharmacology 35:1-12, SAGE Publishing, United States (Mar. 2021).
Tompa, D.R., et al., "Trends and Strategies to Combat Viral Infections: A Review on FDA Approved Antiviral Drugs," International Journal of Biological Macromolecules 172:524-541, Elsevier, Netherlands (Mar. 2021).
Koshkin, A.A., et al., "LNA (Locked Nucleic Acids): Synthesis of the Adenine, Cytosine, Guanine, 5-methylcytosine, Thymine and Uracil Bicyclonucleoside Monomers, Oligomerisation and Unprecedented Nucleic Acid Recognition," Tetrahedron 54:3607-3630, Pergamon Press, United Kingdom (Apr. 1998).
Kroschwitz, J.I., ed., "Polynucleotides," in Concise Encyclopedia of Polymer Science and Engineering, pp. 858-859, John Wiley & Sons, Hoboken, United States (1990).
Kumar, R., et al., "The First Analogues of LNA (Locked Nucleic Acids): Phosphorothioate-LNA and 2'-thio-LNA," Bioorganic & Medicinal Chemistry Letters 8(16):2219-2222, Elsevier Science Limited, United Kingdom (Aug. 1998).
Wan, W.B., et al., "Synthesis, Biophysical Properties and Biological Activity of Second Generation Antisense Oligonucleotides Containing Chiral Phosphorothioate Linkages," Nucleic Acids Research 42(22):13456-13468, Oxford University Press, United Kingdom (Dec. 2014).
Meyer, D., et al., "Identification of the First Synthetic Inhibitors of the Type II Transmembrane Serine Protease TMPRSS2 Suitable for Inhibition of Influenza Virus Activation," The Biochemical Journal 452(2):331-343, Portland Press on behalf of the Biochemical Society, United Kingdom (Jun. 2013).
National Institutes of Allergy and Infectious Diseases, "Coronaviruses," niaid.nih.gov, 2022, accessed at https://www.niaid.nih.gov/diseases-conditions/coronaviruses, 4 Pages.
Oka, N., et al., "An Oxazaphospholidine Approach for the Stereocontrolled Synthesis of Oligonucleoside Phosphorothioates," Journal of the American Chemical Society 125(27):8307-8317, American Chemical Society, United States (Jul. 2003).
Ou, X., et al., "Characterization of Spike Glycoprotein of SARS-CoV-2 on Virus Entry and Its Immune Cross-reactivity With SARS-CoV," Nature Communications 11:1620, Springer Nature, Germany (Apr. 2021).
Park, B.S., et al., "Structure-based Optimization and Biological Evaluation of Trisubstituted Pyrazole as a Core Structure of Potent ROS1 Kinase Inhibitors," Bioorganic & Medicinal Chemistry 22(15):3871-3878, Elsevier Science, United Kingdom (Aug. 2014).
Paszti-Gere, E., et al., "In Vitro Characterization of TMPRSS2 Inhibition in IPEC-J2 Cells," Journal of Enzyme Inhibition and Medicinal Chemistry 31(Suppl 2):123-129, Taylor & Francis, United Kingdom (Nov. 2016).
Rensi, S., et al., "Homology Modeling of TMPRSS2 Yields Candidate Drugs That May Inhibit Entry of SARS-CoV-2 Into Human Cells," ChemRxiv, 12009582, pp. 1-22, Cambridge University Press, United Kingdom (Mar. 2020).
Riva, L., et al., "A Large-scale Drug Repositioning Survey for SARS-CoV-2 Antivirals," BioRxiv, 2020.04.16.044016, pp. 1-43, Cold Spring Harbor Laboratory Press, United States (Apr. 2020).
Rizopoulos, Z., et al., "Vaccinia Virus Infection Requires Maturation of Macropinosomes," Traffic 16(8):814-831, Wiley, United Kingdom (Aug. 2015).
Sanghvi, Y.S., "Chapter 15: Heterocycle Base Modifications in Nucleic Acids and their Applications in Antisense Oligonucleotides," in Antisense Research and Applications, Crooke, S. T., and Lebien, B., Eds., pp. 273-288, CRC Press, United States (1993).
Shi, Y., et al., "Haploinsufficiency Leads to Neurodegeneration in C9ORF72 ALS/FTD Human Induced Motor Neurons," Nature Medicine 24(3):313-325, Springer, Germany (Mar. 2018).
Singh, S.K., et al., "LNA (locked nucleic acids): Synthesis and High-affinity Nucleic acid Recognition," Chemical Communication 4:455-456, Royal Society of Chemistry, United States (1998).
Singh, S.K., et al., "Synthesis of 2'-Amino-LNA: A Novel Conformationally Restricted High-Affinity Oligonucleotide Analogue with a Handle," Journal of Organic Chemistry 63(26): 10035-10039, American Chemical Society, United States (Dec. 1998).
Srivastava, P., et al., "Five- and Six-membered Conformationally Locked 2',4'-carbocyclic Ribo-thymidines: Synthesis, Structure, and Biochemical Studies," Journal of the American Chemical Society 129(26):8362-8379, American Chemical Society, United States (Jul. 2007).
Tang, T., et al., "Coronavirus Membrane Fusion Mechanism Offers a Potential Target for Antiviral Development," Antiviral Research 178:104792, Elsevier, Netherlands (Jun. 2020).
Aleem, A., et al., "Emerging Variants of SARS-CoV-2 and Novel Therapeutics Against Coronavirus (COVID-19)," StatPearls, NCBI Bookshelf, last updated on May 8, 2023, accessed at https://www.ncbi.nlm.nih.gov/books/NBK570580/, accessed on Apr. 11, 2025, 23 pages.
Morgan, K.K., and Seed, S., "Covid Variants," WebMD, last updated on Nov. 15, 2023, accessed at https://www.webmd.com/covid/coronavirus-strains#1, accessed on Apr. 11, 2025, 4 pages.
PubChem, "N-(6-amino-2-propan-2-ylsulfanylpyrimidin-4-yl)-4-tert-butylbenzamide," CID 22349769, Create date: Dec. 5, 2007, accessed at https://pubchem.ncbi.nim.nih.gov/compound/22349769, accessed on May 3, 2025, 8 pages.
American Veterinary Medical Association, "African swine fever," AVMA, accessed at https://www.avma.org/resources-tools/animal-health-and-welfare/animal-health/african-swine-fever, accessed on Jun. 30, 2025, 3 pages.
Boehringer Ingelheim Animal Health USA, "African swine fever: 5 questions and answers," Boehringer Ingelheim, accessed at https://www.boehringer-heim.com/us/animal-health/trends-insights/african-swine-fever-important-facts-boehringer-ingelheim-us, accessed on Jun. 30, 2025, 4 pages.
Department of Homeland Security, "African Swine Fever Virus: An Emerging Transboundary Threat," DHS.gov, accessed at https://www.dbs.gov/sites/default/files/2024-01/23_1116_st_african_swine_fever_virus_factsheet.pdf, accessed on Jun. 30, 2025, 1 page.
World Organisation for Animal Health, "African Swine Fever," WOAH Technical Disease Card: African swine fever, accessed at https://www.woah.org/app/uploads/2021/03/a-african-swine-fever-v2-0.pdf, accessed on Jun. 30, 2025, 6 pages.

* cited by examiner

PIKfyve KINASE INHIBITORS

CROSS-REFERENCE TO EARLIER FILED APPLICATIONS

This patent application is a continuation of U.S. patent application Ser. No. 16/641,159, filed Feb. 21, 2020, which is a 371 application of International Patent Application Serial No. PCT/US2018/048369, filed Aug. 28, 2018, which claims the benefit of U.S. Provisional Patent Application Ser. No. 62/551,047, filed Aug. 28, 2017. The entire contents of each of the above-referenced patent applications are incorporated herein by reference.

STATEMENT OF GOVERNMENT SUPPORT

This invention was made with government support under NS105156 awarded by the National Institutes of Health. The government has certain rights in the invention.

FIELD OF THE INVENTION

The present invention relates to compounds useful as inhibitors of phosphatidylinositol-3-phosphate 5-kinase (PIKfyve).

BACKGROUND OF THE INVENTION

Apilimod is recognized as a potent transcriptional inhibitor of IL-12 and IL-23. See Wada et al., *Blood* 109 (2007): 1156-1164. IL-12 and IL-23 are inflammatory cytokines normally produced by immune cells, such as B-cells and macrophages, in response to antigenic stimulation. Autoimmune disorders and other disorders characterized by chronic inflammation are characterized in part by inappropriate production of these cytokines. In immune cells, the selective inhibition of IL-12/IL-23 transcription by apilimod was recently shown to be mediated by apilimod's direct binding to phosphatidylinositol-3-phosphate 5-kinase (PIKfyve). See Cai et al., *Chemistry and Biol.* 20 (2013):912-921. PIKfyve plays a role in Toll-like receptor signaling, which is important in innate immunity.

Based upon its activity as an immunomodulatory agent and a specific inhibitor of IL-12/IL-23, apilimod has been proposed as useful in treating autoimmune and inflammatory diseases and disorders. See U.S. Pat. Nos. 6,858,606 and 6,660,733 (describing a family of pyrimidine compounds, including apilimod, purportedly useful for treating diseases and disorders characterized by IL-12 or IL-23 overproduction, such as rheumatoid arthritis, sepsis, Crohn's disease, multiple sclerosis, psoriasis, or insulin dependent diabetes mellitus). Similarly, apilimod was suggested to be useful for treating certain cancers based upon its activity to inhibit c-Rel or IL-12/23, particularly in cancers where these cytokines were believed to play a role in promoting aberrant cell proliferation. See WO 2006/128129 and Baird et al., *Frontiers in Oncology* 3:1 (2013, respectively). International Publication No. WO 2016/210372 and U.S. Patent Publication No. 2018/0161335, which are hereby incorporated by reference, disclose methods of treating a neurological disease such as amyotrophic lateral sclerosis with a PIKFYVE kinase inhibitor.

SUMMARY OF THE INVENTION

The present invention is directed to a compound of the formula (I)

(I)

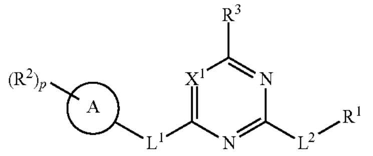

or a pharmaceutically acceptable salt thereof, wherein $R^1$ is hydroxy, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

each occurrence of $R^2$ is independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted heterocyclyl;

$R^3$ is a nitrogen- or oxygen-containing moiety;

Ring A is (i) a 5 or 6-membered heteroaryl or 5-6 or 6-5 membered bicyclic heteroaryl, each having at least one nitrogen or oxygen ring atom, or (ii) phenyl;

$L^1$ is absent, $C_1$-$C_2$ alkylene, —$NR^c$—, —O—, —S—, —C(O)—, —NHC(O)—, or —C(O)NH—;

$L^2$ is —O—$(CR^aR^b)_m$—, —$(CR^aR^b)_m$—, —$NR^c$—$(CR^aR^b)_m$—, or —S—$(CR^aR^b)_m$—;

$X^1$ is CH, N, or $CR^c$;

each occurrence of $R^a$ and $R^b$ are independently hydrogen, hydroxy, hydroxy$(C_{1-4})$alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —$C(O)R^d$, —$C(S)R^d$, —$OC(O)R^d$, —$SC(O)R^d$, $OC(S)R^d$, $SC(S)R^d$, —$NR^cC(O)R^d$, —$NR^cC(S)R^d$, —$SO_2R^c$, —$S(O)R^c$, —$NR^cSO_2R^d$, —$OS(O)_2R^d$, —$OP(O)R^dR^e$, or —$P(O)R^dR^e$;

$R^c$ is a hydrogen or $C_{1-6}$ alkyl (e.g., $C_1$-$C_4$ alkyl);

each occurrence of $R^d$ and $R^e$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

m is 1-4; and p is 1 or 2.

These compounds are useful as PIKfyve kinase inhibitors.

In one embodiment, $R^1$ is heterocyclyl or heteroaryl. For example, $R^1$ may be selected from (the squiggly lines indicate the point of attached to the rest of the molecule)

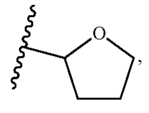, 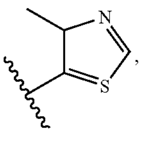, 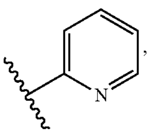,

-continued

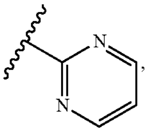, and 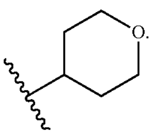.

In another embodiment, $R^1$ is hydroxy.

In one embodiment, each occurrence of $R^2$ is independently substituted or unsubstituted aryl, such as a substituted or unsubstituted phenyl. For instance, $R^2$ may be phenyl, a halogen-substituted phenyl, an alkyl-substituted phenyl (e.g., a $C_{1-4}$ alkyl-substituted phenyl), a halogenated alkyl-substituted phenyl, or an alkoxy-substituted phenyl. In one embodiment, $R^2$ is selected from phenyl, 3-methoxyphenyl, 3-methylphenyl, 3-trifluoromethylphenyl, and 3-chlorophenyl. In a preferred embodiment, $R^2$ is selected from phenyl, 3-methoxyphenyl, and 3-methylphenyl.

In another embodiment, each occurrence of $R^2$ is independently substituted or unsubstituted alkyl (such as a $C_{1-4}$ alkyl). For instance, $R^2$ can be unsubstituted isopropyl.

In one embodiment, $R^3$ is a substituted or unsubstituted, saturated or unsaturated nitrogen- or oxygen-containing heterocyclyl. For instance, $R^3$ can be a substituted or unsubstituted, saturated or unsaturated 5-10 membered (such as a 5-8 membered) mono- or bicyclic heterocyclyl having at least one nitrogen or oxygen ring atom. In one embodiment, $R^3$ is a substituted or unsubstituted 5-10 membered (such as a 5-8 membered) mono- or bi-cyclic heterocyclyl having at least one nitrogen atom and optionally an oxygen ring atom, where the nitrogen ring atom is directly attached to the rest of the molecule. In one preferred embodiment, $R^3$ is a substituted or unsubstituted (unsaturated) 5-membered monocyclic heterocyclyl having an oxygen ring atom or a nitrogen ring atom.

In another embodiment, $R^3$ is a substituted or unsubstituted, saturated or unsaturated 6-membered monocyclic heterocyclyl having an oxygen ring atom and optionally a nitrogen ring atom. In yet another embodiment, $R^3$ is a saturated 8-membered bicyclic heterocyclyl having a nitrogen ring atom and an oxygen ring atom. In one embodiment, $R^3$ is selected from

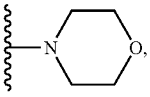, 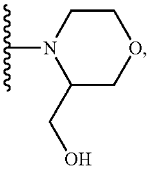, 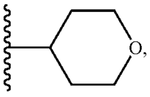,

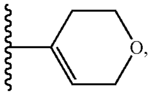, 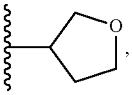, 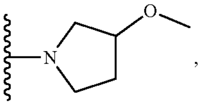,

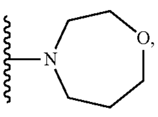, 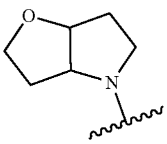, 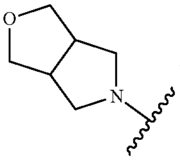,

-continued

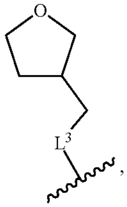, 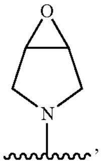, 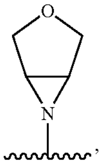, 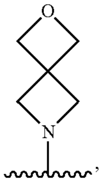,

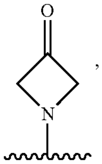, 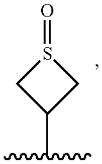, 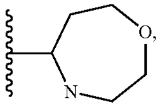, and

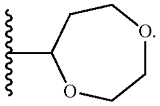.

In one preferred embodiment, $R^3$ is selected from

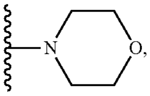, 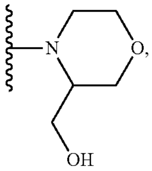, 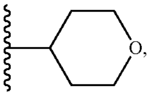,

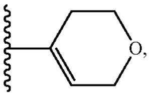, 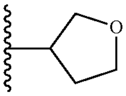, 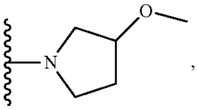,

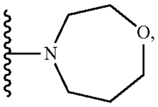, and 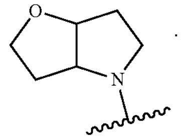.

In another preferred embodiment, $R^3$ is

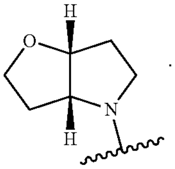 [SMILES: *N1CC[C@H]2OCC[C@H]21].

In yet another embodiment, $R^3$ is a sulfonyl group of the formula —$S(O)(CH_2)_qOR^4$, where $R^4$ is hydrogen or $C_1$-$C_4$ alkyl and q is 1-4.

In one embodiment, ring A is a 5-membered heteroaryl having at least one nitrogen ring atom. In one preferred embodiment, ring A includes two heteroatoms as ring atoms (such as two nitrogen ring atoms, or one nitrogen ring atom with one sulfur ring atom). In another preferred embodiment, ring A is selected from

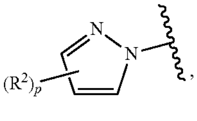, 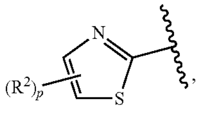, and

-continued

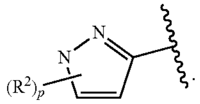

For instance, ring A can be selected from

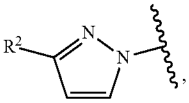,
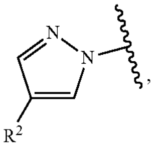,
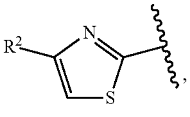, and
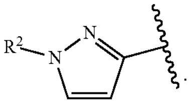.

In one preferred embodiment, the $R^2$ group in ring A above is selected from substituted or unsubstituted aryl, such as a substituted or unsubstituted phenyl. For instance, $R^2$ may be phenyl, an alkyl-substituted, or an alkoxy-substituted phenyl. In a preferred embodiment, $R^2$ is selected from phenyl, 3-methoxyphenyl, and 3-methylphenyl.

In one embodiment, $L^1$ is absent.

In another embodiment, $L^1$ is —NH—, —N($CH_3$)—, —O—, or —$CH_2$—. In one embodiment, $L^1$ is —NH—. In another embodiment, $L^1$ is —C(O)NH— (where the carbonyl is attached to the rest of the molecule and the nitrogen is attached to ring A). In yet another embodiment, $L^1$ is —NHC(O)— (where the nitrogen atom is attached to the rest of the molecule and the carbonyl is attached to ring A).

In one embodiment, $L^2$ is —O—$(CR^aR^b)_m$—. In one preferred embodiment, $L^2$ is —$OCH_2CH_2$— or —$OCH_2$—. In another embodiment, $L^2$ is —$OCH_2CH_2CH(OH)CH_2$—.

In another embodiment, $L^2$ is —$(CR^aR^b)_m$—. In one preferred embodiment, $L^2$ is —$CH_2CH_2$—.

In yet another embodiment, $L^2$ is —$NR^c$—$(CR^aR^b)_m$—, such as —NH—$(CR^aR^b)_m$— (e.g., —NH—, —$NHCH_2$—, and —$NHCH_2CH_2$—).

In one embodiment, -$L^2$-$R^1$ is —$OCH_2CH_2CH(OH)CH_2OH$.

In one preferred embodiment, $X^1$ is CH. In another embodiment, $X^1$ is N.

In one embodiment, each occurrence of $R^a$ and $R^b$ are independently hydrogen, hydroxy, or hydroxy($C_{1-4}$)alkyl. In another embodiment, each occurrence of $R^a$ and $R^b$ are independently hydrogen or hydroxy.

In one embodiment, m is 1. In another embodiment, m is 2. In a preferred embodiment, m is 1 or 2 when $R^1$ is cyclic. In another preferred embodiment, m is 3 or 4 when $R^1$ is acyclic.

In a preferred embodiment, p is 1.

In another embodiment, p is 2.

In one preferred embodiment, the moiety

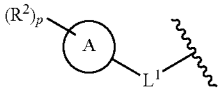

is selected from

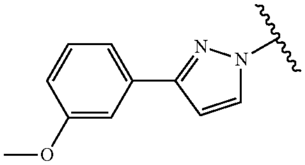
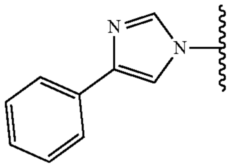
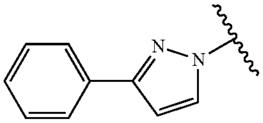
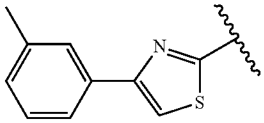
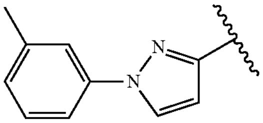
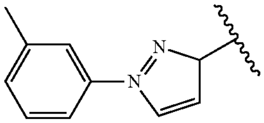
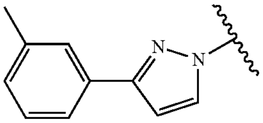
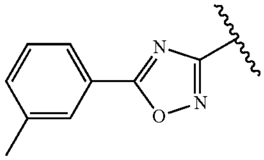
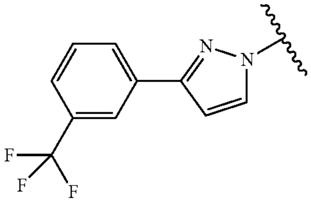
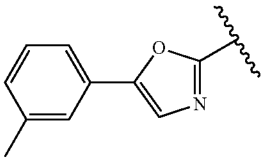
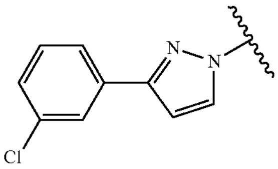
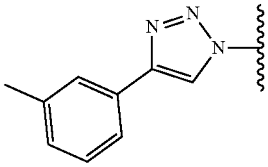
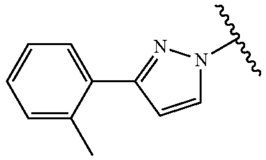
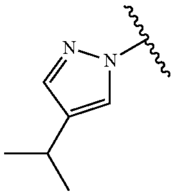
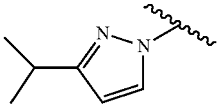
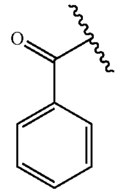
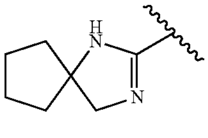
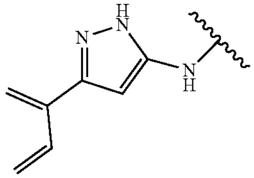
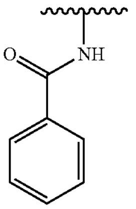
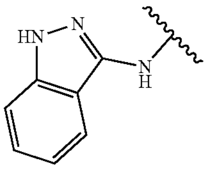
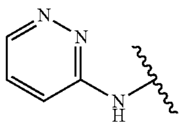

-continued

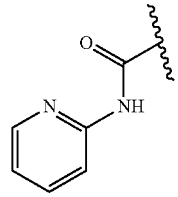 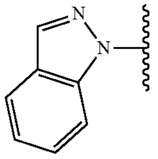 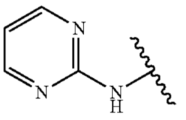

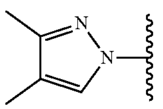 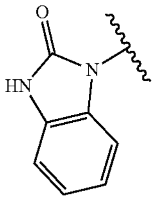 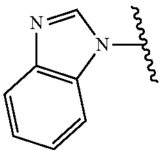

Another embodiment is a compound of the formula (II)

(II)

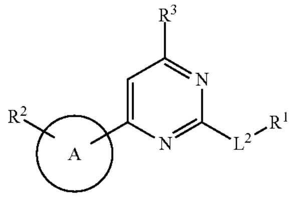

or a pharmaceutically acceptable salt thereof, wherein $R^1$ is hydroxy, substituted or unsubstituted heteroaryl, or substituted or unsubstituted heterocyclyl;

$R^2$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted heterocyclyl;

$R^3$ is a substituted or unsubstituted oxygen-containing heterocyclyl;

Ring A is a 5-membered heteroaryl having at least one nitrogen ring atom;

$L^2$ is $—O—(CR^aR^b)_m—$;

each occurrence of $R^a$ and $R^b$ are independently hydrogen, hydroxy, or hydroxy$(C_{1-4})$alkyl; and m is 1-4.

In one embodiment of the compound of formula (II), $R^1$ is heterocyclyl or heteroaryl. For example, $R^1$ may be selected from

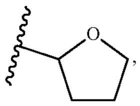, 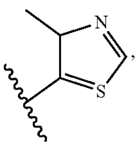, 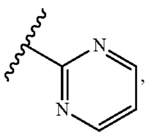, and

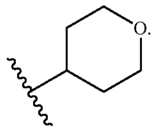

In one embodiment of the compound of formula (II), $R^2$ is substituted phenyl, such as an alkoxy-substituted phenyl, halogen-substituted phenyl, or alkyl-substituted phenyl. For example, $R^2$ can be methoxyphenyl (e.g., 3-methoxyphenyl) or methylphenyl (e.g., 3-methylphenyl).

In another embodiment of the compound of formula (II), $R^2$ is hydroxy.

In one preferred embodiment of the compound of formula (II), $R^3$ is selected from

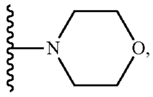 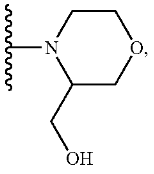 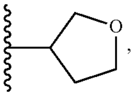, and

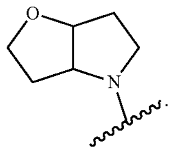

In another preferred embodiment, $R^3$ is

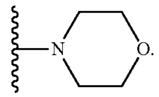 [SMILES: *N1CCOCC1]

In another preferred embodiment, $R^3$ is

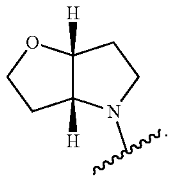 [SMILES: *N1CC[C@H]2OCC[C@H]21]

In one embodiment of the compound of formula (II), ring A is a 5-membered heteroaryl having (i) two nitrogen ring atoms or (ii) one nitrogen ring atom and one sulfur ring atom. In another embodiment, ring A is selected from

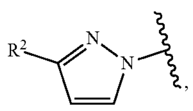, 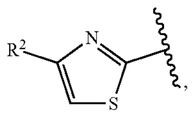, and

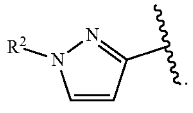

In one embodiment of the compound of formula (II), $L^2$ is $—OCH_2—$, $—OCH_2CH_2—$, $—OCH_2CH_2CH(OH)CH_2—$, or $—CH_2CH_2—$. In one preferred embodiment, $L^2$ is $—OCH_2—$, $—OCH_2CH_2—$, or $—OCH_2CH_2CH(OH)CH_2—$.

Exemplary compounds of the present include those listed below and pharmaceutically salts thereof.

-continued
1
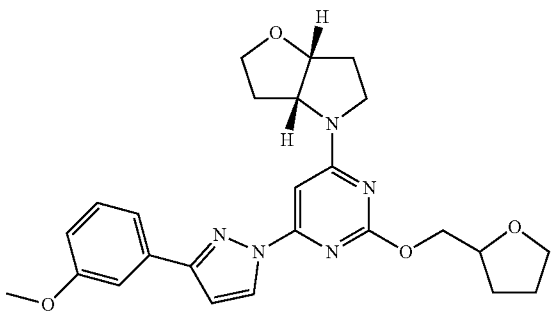
2
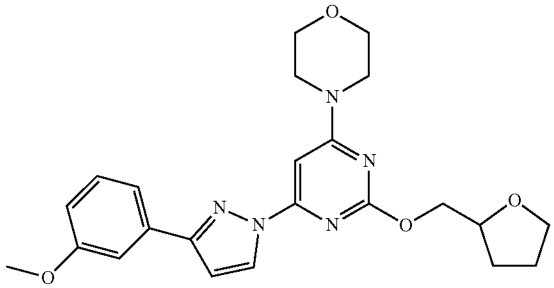
3
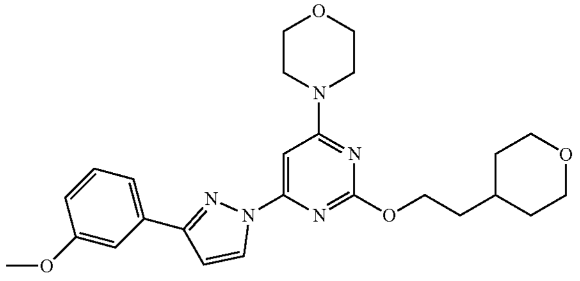
4
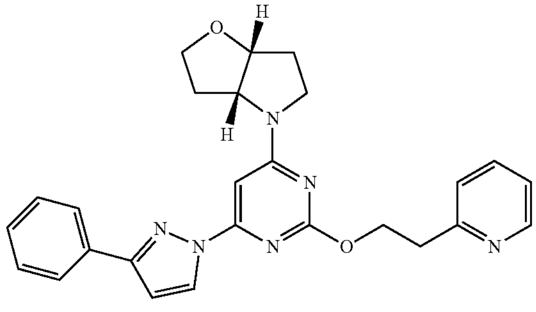
5
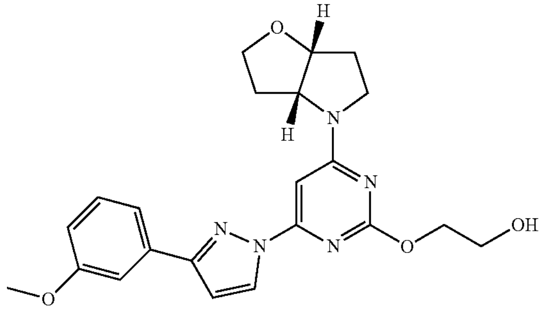
6
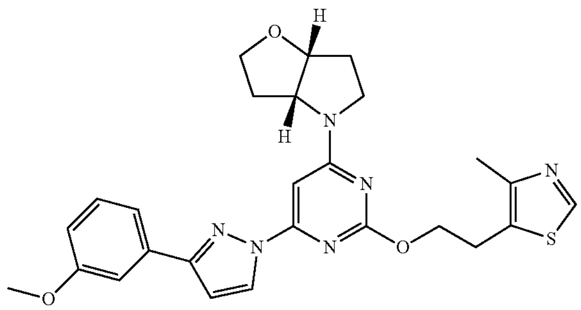
7
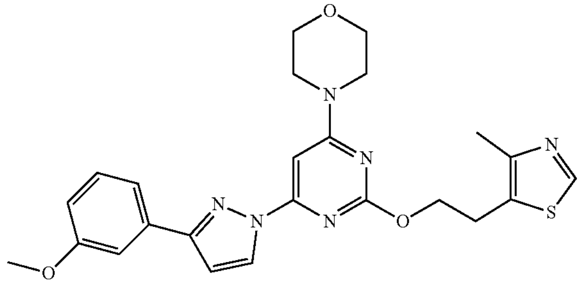
8
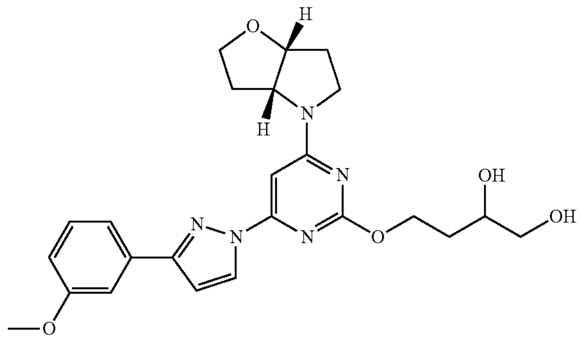
9
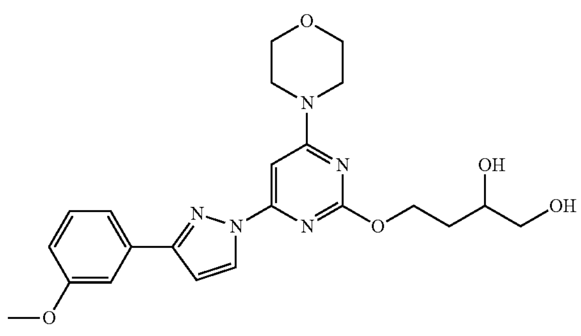

-continued
10
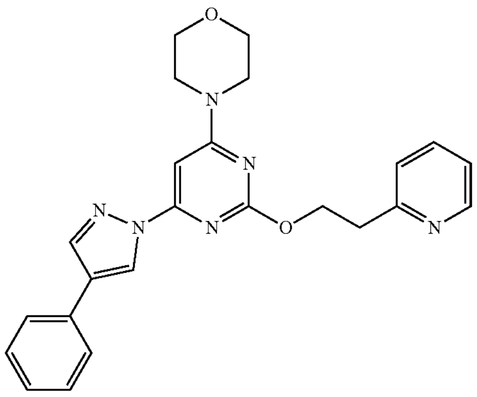
11
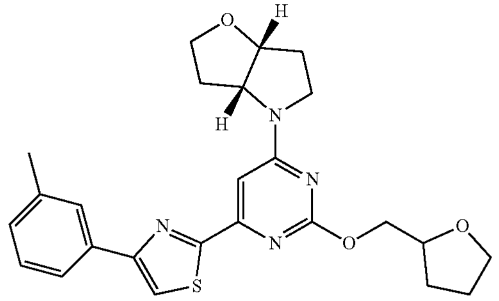
12
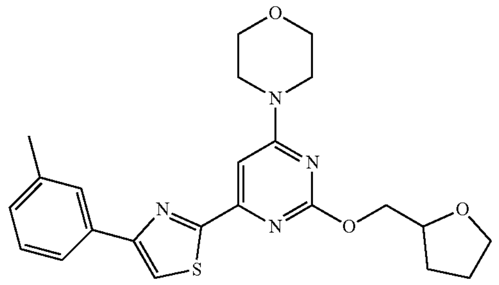
13
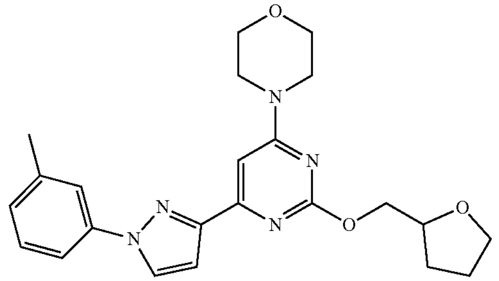
14
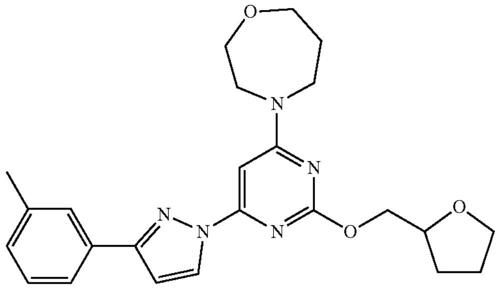
-continued
15
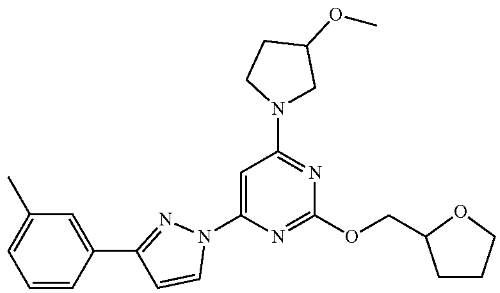
16
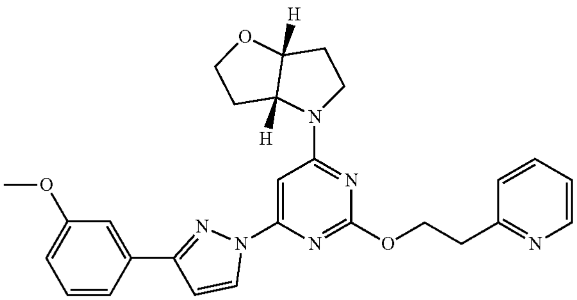
17
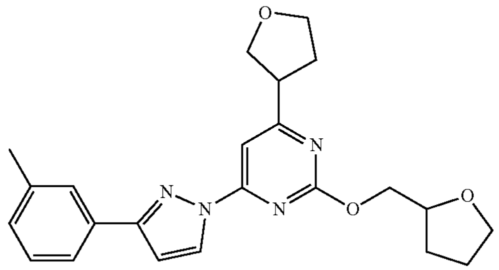
18
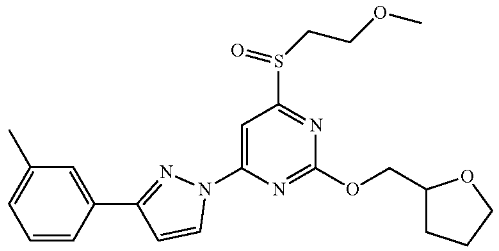
19
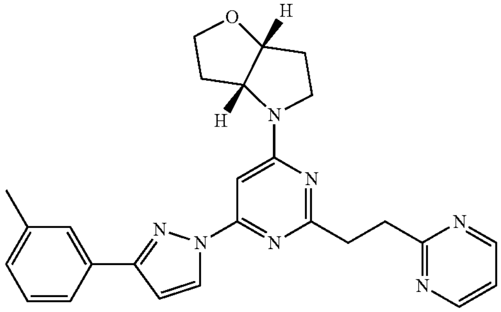

-continued

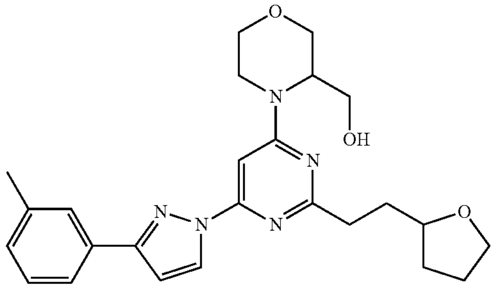

Another embodiment is a method of inhibiting PIKfyve in a subject (such as a human subject) in need thereof comprising administering an effective amount of a compound of the present invention.

Yet another embodiment is a method for treating a disease or disorder associated with PIKfyve in a human subject in need thereof comprising administering an effective amount of a compound of the present invention to the subject.

Yet another embodiment is a method of treating a subject having a neurological disease comprising administering to the subject an effective amount of a compound of the present invention to the subject. In one embodiment, the neurological disease is amyotrophic lateral sclerosis (ALS). In another embodiment, the neurological disease is frontotemporal dementia (FTD). In yet another embodiment, the neurological disease is Alzheimer's disease. In yet another embodiment, the neurological disease is Parkinson's disease. In yet another embodiment, the neurological disease is Huntington's disease. In yet another embodiment, the neurological disease is Charcot-Marie-Tooth disease (CMT).

In one embodiment, the effective amount of the compound is the amount effective to inhibit cellular PIKfyve activity in target cells in the subject. In another embodiment, the effective amount is the amount effective to induce vacuolization and disrupts intracellular trafficking in target cells.

In one embodiment, the target cell is a cancer cell. In one embodiment, the cancer cell is a lymphoma cell. In one embodiment, the lymphoma cell is a non-Hodgkin's lymphoma cell.

In one embodiment, the disease of disorder is selected from a cancer, a viral infection, or a cell proliferative disorder. For example, the cancer can be a lymphoma or melanoma. In one embodiment, the cancer is refractory or resistant to standard therapy. In one embodiment, the cancer is a non-Hodgkin's lymphoma.

One embodiment is a method of treating a viral infection in a subject in need thereof comprising administering an effective amount of a compound of the present invention to the subject. The viral infection can be caused by any type of virus such as RNA and DNA viruses. In one embodiment, the virus is Ebola virus. In another embodiment, the virus is middle east respiratory syndrome virus (MERS). In yet another embodiment, the virus is JC polyomavirus (JC). In yet another embodiment, the virus is BK polyomavirus (BK). In yet another embodiment, the virus is Herpes Simplex Virus (HSV). In yet another embodiment, the virus is Marburg virus (MarV). In yet another embodiment, the virus is Venezuelan equine encephalitis virus (VEEV). In yet another embodiment, the virus is Lymphocytic choriomeningitis virus (LCMV).

Another embodiment is method of treating Charcot-Marie-Tooth disease (CMT) in a subject, preferably a human subject, in need of such treatment, by administering an effective amount of a compound of the present invention to the subject.

One embodiment is a method for treating a lymphoma comprising administering (e.g., an effective amount of) a compound of the present invention and at least one additional active agent. In one embodiment, the at least one additional active agent is selected from ibrutinib, rituximab, doxorubicin, prednisolone, vincristine, velcade, and everolimus, and combinations thereof. In one embodiment, the method includes a therapeutic regimen comprising administering a compound of the present invention and a CHOP regimen.

In one embodiment, the method is a method for treating melanoma and the method further comprises administering at least one additional active agent to the subject in a therapeutic regimen comprising a compound of the present invention and the at least one additional active agent. In one embodiment, the at least one additional active agent is selected from dacarbazine, temozolomide, Nab-paclitaxel, carmustine, cisplatin, carboplatin, or vinblastine.

In one embodiment, the method is a method for treating a viral infection and the method further comprises administering at least one additional active agent to the subject in a therapeutic regimen comprising a compound of the present invention and the at least one additional active agent. In one embodiment, the at least one additional active agent is selected from selected from the group consisting of apilimod, APY0201, and YM-201636.

In accordance with any of the methods described herein, a compound of the present invention may also be administered in combination with a non-therapeutic agent which mitigates one or more side effects associated with the compound or increases the bioavailability of the compound. In one embodiment, the non-therapeutic agent is selected from the group consisting of ondansetron, granisetron, dolasetron and palonosetron. In another aspect, the non-therapeutic agent is selected from the group consisting of pindolol and risperidone. In another aspect, the non-therapeutic agent is selected from a cytochrome P450 3A (CYP3A) inhibitor. In one embodiment, the CYP3A inhibitor is selected from ritonavir and cobicistat.

In one embodiment, the viral infection is caused by a virus selected from the group consisting of measles, Ebola (EboV), Marburg (MarV), borna disease, and human immunodeficiency virus (HIV), severe acute respiratory system virus (SARS), and middle east respiratory syndrome virus (MERS). In one embodiment, the viral infection is caused by an EboV virus.

In one embodiment, the compound is in the form a pharmaceutical composition comprising the compound and at least one pharmaceutically acceptable carrier.

In one embodiment, the compound comprises at least 95% or at least 99% enantiomeric excess of the (R)-enantiomer. In one embodiment, the compound comprises at least 95% or at least 99% enantiomeric excess of the (S)-enantiomer.

Another embodiment is pharmaceutical composition comprising a compound of the present invention wherein the compound comprises at least 95% or at least 99% enantiomeric excess of the (R)-enantiomer or the (S)-enantiomer.

DETAILED DESCRIPTION OF THE INVENTION

Definitions

As used herein the following definitions shall apply unless otherwise indicated. Further, many of the groups defined herein can be optionally substituted. The listing of substituents in the definition is exemplary and is not to be construed to limit the substituents defined elsewhere in the specification.

The term "alkyl", unless otherwise specified, refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl group as defined above having up to 6 carbon atoms. The term "$C_{1-3}$ alkyl" refers to an alkyl group as defined above having up to 3 carbon atoms. In appropriate circumstances, the term "alkyl" refers to a hydrocarbon chain radical as mentioned above which is bivalent.

The term "alkenyl", unless otherwise specified, refers to an aliphatic hydrocarbon group containing one or more carbon-carbon double bonds and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl. The term "$C_{2-6}$ alkenyl" refers to an alkenyl group as defined above having up to 6 carbon atoms. In appropriate circumstances, the term "alkenyl" refers to a hydrocarbon group as mentioned above which is bivalent.

The term "alkynyl", unless otherwise specified, refers to a straight or branched chain hydrocarbyl radical having at least one carbon-carbon triple bond, and having in the range of 2 to up to 12 carbon atoms (with radicals having in the range of 2 to up to 10 carbon atoms presently being preferred) e.g., ethynyl, propynyl, and butnyl. The term "$C_{2-6}$ alkynyl" refers to an alkynyl group as defined above having up to 6 carbon atoms. In appropriate circumstances, the term "alkynyl" refers to a hydrocarbyl radical as mentioned above which is bivalent.

The term "alkoxy" unless otherwise specified, denotes an alkyl, cycloalkyl, or cycloalkylalkyl group as defined above attached via an oxygen linkage to the rest of the molecule. The term "substituted alkoxy" refers to an alkoxy group where the alkyl constituent is substituted (i.e., -0-(substituted alkyl). For example "alkoxy" refers to the group —O-alkyl, including from 1 to 8 carbon atoms of a straight, branched, cyclic configuration and combinations thereof attached to the parent structure through an oxygen atom. Examples include methoxy, ethoxy, propoxy, isopropoxy, cyclopropyloxy, and cyclohexyloxy. In appropriate circumstances, the term "alkoxy" refers to a group as mentioned above which is bivalent.

The term "cycloalkyl", unless otherwise specified, denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and spirobicyclic groups, e.g., spiro (4,4) non-2-yl. The term "$C_{3-6}$ cycloalkyl" refers to a cycloalkyl group as defined above having up to 6 carbon atoms.

The term "cycloalkylalkyl", unless otherwise specified, refers to a cyclic ring-containing radical containing in the range of about 3 up to 8 carbon atoms directly attached to an alkyl group which is then attached to the main structure at any carbon from the alkyl group, such as cyclopropylmethyl, cyclobutylethyl, and cyclopentylethyl.

The term "cycloalkenyl", unless otherwise specified, refers to cyclic ring-containing radicals containing in the range of about 3 up to 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which is then attached to the main structure at any carbon from the alkyl group.

The term "aryl", unless otherwise specified, refers to aromatic radicals having in the range of 6 up to 20 carbon atoms such as phenyl, naphthyl, tetrahydronaphthyl, indanyl, and biphenyl.

The term "arylalkyl", unless otherwise specified, refers to an aryl group as defined above directly bonded to an alkyl group as defined above, e.g., $—CH_2C_6H_5$ and $—C_2H_5C_6H_5$.

The term "heterocyclic ring", unless otherwise specified, refers to a non-aromatic 3 to 15 member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom.

The term "heterocyclyl", unless otherwise specified, refers to a heterocylic ring radical as defined above. The heterocyclyl ring radical may be attached to the main structure at any heteroatom or carbon ring atom. In appropriate circumstances, the term "heterocyclyl" refers to a hydrocarbon chain radical as mentioned above which is bivalent.

The term "heterocyclylalkyl", unless otherwise specified, refers to a heterocylic ring radical as defined above directly bonded to an alkyl group. The heterocyclylalkyl radical may be attached to the main structure at any carbon atom in the alkyl group. Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl", unless otherwise specified, refers to an optionally substituted 5 to 14 member aromatic ring having one or more heteroatoms selected from N, O, and S as ring atoms. The heteroaryl may be a mono-, bi- or tricyclic ring system. Examples of such "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamo holinyl, thiamorpholinyl sulfoxide, thiamo holinyl sulfone, dioxaphospholanyl, oxadiazolyl, chromanyl, and isochromanyl.

The term "5 or 6-membered heteroaryl" refers to a heteroaryl having 5- or 6-ring atoms. The term "5-6 or 6-5 membered bicyclic heteroaryl" refers to a bicyclic heteroaryl with a five-membered ring fused to a six-membered ring, where the 5-membered ring is bound to the rest of the molecule (referred as a "5-6 membered bicyclic heteroaryl") or the 6-membered ring is bound to the rest of the molecule (referred as a "6-5 membered bicyclic heteroaryl").

The heteroaryl ring radical may be attached to the main structure at any heteroatom or carbon atom. The term "substituted heteroaryl" also includes ring systems substituted with one or more oxide (—O—) substituents, such as pyridinyl N-oxides.

The term "heteroarylalkyl", unless otherwise specified, refers to a heteroaryl ring radical as defined above directly bonded to an alkyl group. The heteroarylalkyl radical may be attached to the main structure at any carbon atom from alkyl group.

The term "cyclic ring" refers to a cyclic ring containing 3 to 10 carbon atoms.

The term "substituted" unless otherwise specified, refers to substitution with any one or any combination of the following substituents which may be the same or different and are independently selected from hydrogen, hydroxy, halogen, carboxyl, cyano, nitro, oxo (═O), thio (═S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, $—COOR^x$, $—C(O)R^x$, —C(S)RX, $—C(O)NR^xR^y$, $—C(O)ONR^xR^y$, $—NR^yR^z$, $—NR^xCONR^yR^z$, $—N(R^x)SOR^y$, $—N(R^x)SO_2R^y$, $═N—NR^xR^y$, $—NR^xC(O)OR^y$, $—NR^xR^y$, $—NR^xC(O)R^y$, $—NR^xC(S)R^y$ $—NR^xC(S)NR^yR^z$, $—SONR^xR^y$, $—SO_2NR^xR^y$, $—OR^x$, $—OR^xC(O)NR^yR^z$, $—OR^xC(O)OR^y$, $—OC(O)R^x$, $—OC(O)NR^xR^y$, $—R^xNR^yC(O)R^z$, $—R^xOR^y$, $—R^xC(O)OR^y$, $—R^xC(O)NR^yR^z$, $—R^xC(O)R^x$, $—R^xOC(O)R^y$, $—SR^x$, $—SOR^x$, $—SO_2R^x$, and $—ONO_2$, wherein $R^x$, $R^y$ and $R^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted heteroaryl, substituted or unsubstituted heteroarylalkyl, substituted or unsubstituted heterocyclic ring, or substituted heterocyclylalkyl ring, or any two of $R^x$, $R^y$ and $R^z$ may be joined to form a substituted or unsubstituted saturated or unsaturated 3-10 membered ring, which may optionally include heteroatoms which may be the same or different and are selected from O, $NR^x$ (e.g., $R^x$ can be hydrogen or $C_{1-6}$ alkyl) or S. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted. For example, when the substituent on "substituted alkyl" is "substituted aryl", the substituent on "substituted aryl" cannot be "substituted alkenyl".

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

Certain of the compounds described herein contain one or more asymmetric centers and can thus give rise to enantiomers, diastereomers, and other stereoisomeric forms that can be defined, in terms of absolute stereochemistry, as (R)— or (S)—. The present chemical entities, pharmaceutical compositions and methods are meant to include all such possible isomers, including racemic mixtures, optically pure forms and intermediate mixtures. Non-limiting examples of intermediate mixtures include a mixture of isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

A "leaving group or atom" is any group or atom that will, under the reaction conditions, cleave from the starting material, thus promoting reaction at a specified site. Suitable examples of such groups unless otherwise specified are halogen atoms and mesyloxy, p-nitrobenzensulphonyloxy and tosyloxy groups.

The term "prodrug" refers to a compound, which is an inactive precursor of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into circulation, thereby effectively increasing the biological half-life of the originally administered compound.

Additionally, the instant invention also includes the compounds which differ only in the presence of one or more isotopically enriched atoms for example replacement of hydrogen with deuterium or tritium, or the replacement of a carbon by $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium, iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, and alkyl sulphates. Salts may include acid addition salts where appropriate which are sulphates, nitrates, phosphates, perchlorates, borates, hydrohalides (e.g., hydrochlorides), acetates, tartrates, maleates, citrates, fumarates, succinates, palmoates, methanesulphonates, benzoates, salicylates, benzenesulfonates, ascorbates, glycerophosphates, and ketoglutarates. Salts can be formed by methods known in the art.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried. In one embodiment, the amount of compound administered ranges from about 0.1 mg to 5 g, from about 1 mg to 2.0 g, from about 100 mg to 1.5 g, from about 200 mg to 1.5 g, from about 400 mg to 1.5 g, and from about 400 mg to 1.0 g.

As used herein, the term "treating" refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

A "subject" includes a mammal. The mammal can be e.g., any mammal, e.g., a human, primate, vertebrate, bird, mouse, rat, fowl, dog, cat, cow, horse, goat, camel, sheep or a pig. Preferably, the mammal is a human. The term "patient" refers to a human subject.

In accordance with the methods described herein, a "subject in need of" is a subject having a disease, disorder or condition, or a subject having an increased risk of developing a disease, disorder or condition relative to the population at large. The subject in need thereof can be one that is "non-responsive" or "refractory" to a currently available therapy for the disease or disorder, for example cancer. In this context, the terms "non-responsive" and "refractory" refer to the subject's response to therapy as not clinically adequate to relieve one or more symptoms associated with the disease or disorder. In one aspect of the methods described here, the subject in need thereof is a subject having cancer whose cancer is refractory to standard therapy or whose cancer has recurred following standard treatment.

Pharmaceutical Compositions

One embodiment is a pharmaceutical composition suitable for use in a subject, such as a human. The pharmaceutical composition may comprise at least one pharmaceutically acceptable excipient or carrier.

The pharmaceutical composition may also include at least one additional active agent, such as an alkylating agent, an intercalating agent, a tubulin binding agent, a corticosteroid, or any combination of any of the foregoing. Examples of additional active agents include, but are not limited to, ibrutinib, rituximab, doxorubicin, prednisolone, vincristine, velcade, and everolimus, In one embodiment, the at least one additional active agent is a therapeutic agent selected from cyclophosphamide, hydroxydaunorubicin (also referred to as doxorubicin) vincristine, prednisone, prednisolone, and any combination of any of the foregoing.

The pharmaceutical composition may include one or more non-therapeutic agents, such as ondansetron, granisetron, dolasetron, palonosetron, pindolol, risperidone, or any combination of any of the foregoing.

A pharmaceutical composition can be provided as a dosage unit form, such as an ampoule, a vial, a suppository, a dragee, a tablet, or a capsule.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

Preparation of the Compounds

The compounds of the present invention may be prepared as follows.

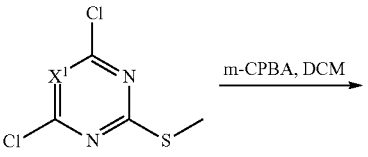

Intermediate A-1

4,6-dichloro-2-(methylsulfonyl)pyrimidine

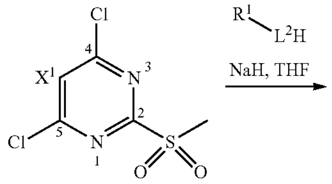

Intermediate 1

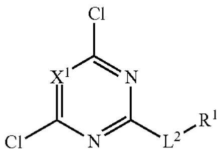

Intermediate A-3

-continued

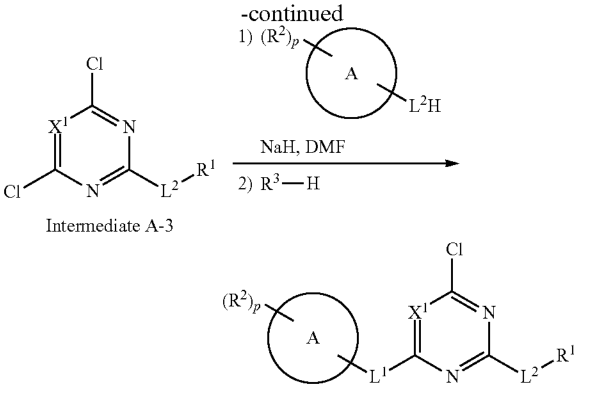

Intermediate A-3

Starting intermediate A-1 is oxidized, for example by reaction with m-CPBA (meta-chloroperoxybenzoic acid) in a solvent, such as dichloromethane, to produce intermediate I. Intermediate I is then reacted with $R^1$-$L^2$H, for example, in the presence of a base (such as NaH) and in a solvent, such as THF, to form Intermediate A-3. Intermediate A-3 is first reacted with

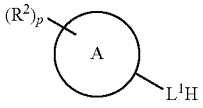

and then with $R^3$—H to form the final compound.

Methods of Treatment

The compounds of the present invention are useful as PIKfyve kinase inhibitors.

One embodiment a method of treating a subject having a neurological disease comprising administering to the subject an effective amount of a compound of the present invention (or a pharmaceutical composition of the present invention) to the subject. In a preferred embodiment, the subject is a human subject. The PIKfyve kinase inhibitors described herein may be used in the methods for treating a neurological disease described in U.S. Patent Publication No. 2018/0161335, which is hereby incorporated by reference in its entirety. For example, the neurological disease may be one that has neuronal death generated by intracellular aggregates.

In certain embodiments, the method includes treating amyotrophic lateral sclerosis (ALS). In certain embodiments, the method includes treating frontotemporal dementia (FTD). In certain embodiments, the method includes treating a neurological disease that is associated with aberrant endosomal trafficking. In certain embodiments, the method includes treating a neurological disease that is associated with aberrant lysosomal trafficking. In further embodiments, the method includes treating a subject who has a $(GGGGCC)_n$ repeat expansion in the C9ORF72 gene. In further embodiments, the subject is haploinsufficient for C9ORF72. In further embodiments the method includes treating patients who have a 50% or greater reduction in C9ORF72 protein activity. In further embodiments, the method includes a C9ORF72 gene product that comprises a dipeptide repeat resulting from the $(GGGGCC)_n$ expansion. In further embodiments, the method includes a gain-of-function or loss of function mutation resulting from the $(GGGGCC)_n$ expansion. In further embodiments, the neurological disease is associated with neuronal hyperexcitability.

One embodiment is a method of treating a subject having amyotrophic lateral sclerosis (ALS) comprising administering to the subject (preferably a human subject) an effective amount of a compound of the present invention to the subject. Another embodiment is a method of treating a subject having frontotemporal dementia (FTD) comprising administering to the subject (preferably a human subject) an effective amount of a compound of the present invention to the subject. Yet another embodiment is a method of treating a subject having Alzheimer's disease comprising administering to the subject (preferably a human subject) an effective amount of a compound of the present invention to the subject. Yet another embodiment is a method of treating a subject having Parkinson's disease comprising administering to the subject (preferably a human subject) an effective amount of a compound of the present invention to the subject. Yet another embodiment is a method of treating a subject having Huntington's disease comprising administering to the subject (preferably a human subject) an effective amount of a compound of the present invention to the subject. Yet another embodiment is a method of treating a subject having Charcot-Marie-Tooth disease (CMT) comprising administering to the subject (preferably a human subject) an effective amount of a compound of the present invention to the subject.

The method may further comprise also administering an effective amount of a potassium channel activator, an inhibitor of a glutamate receptor (such as the receptor NMDA, AMPA, or kainite) (e.g., AP5, CNQX, and NBQX), or any combination of any of the foregoing.

PIKfyve is a phosphoinositide kinase (PIK) that contains a FYVE-type zinc finger domain, which binds phosphatidylinositol 3-phosphate (PI3P). PIKfyve phosphorylates PI3P to produce $PI(3,5)P_2$, which is involved in cellular processes including membrane trafficking and cytoskeletal reorganization. The inhibition of PIKfyve by a compound described herein is useful in treating not only cancer, but also Charcot-Marie-Tooth disease and certain viral infections, such as those caused by a virus selected from measles, Ebola virus (EboV), Marburg virus (MarV), borna disease, and human immunodeficiency virus (HIV), severe acute respiratory system virus (SARS), middle east respiratory syndrome virus (MERS), JC polyomavirus (JC), BK polyomavirus (BK), Herpes Simplex Virus (HSV), Venezuelan equine encephalitis virus (VEEV) and Lymphocytic choriomeningitis virus (LCMV). The viral infection can be caused by any type of virus such as RNA and DNA viruses.

One embodiment is a method of treating a viral infection in a subject in need thereof comprising administering an effective amount of a compound of the present invention to the subject. In one embodiment, the virus is Ebola virus. In another embodiment, the virus is middle east respiratory syndrome virus (MERS). In yet another embodiment, the virus is JC polyomavirus (JC). In yet another embodiment, the virus is BK polyomavirus (BK). In yet another embodiment, the virus is Herpes Simplex Virus (HSV). In yet another embodiment, the virus is Marburg virus (MarV). In yet another embodiment, the virus is Venezuelan equine encephalitis virus (VEEV). In yet another embodiment, the virus is Lymphocytic choriomeningitis virus (LCMV).

One embodiment is a method for treating a cell proliferative disease, a cancer, or a viral infection in a subject, preferably a human subject, in need of such treatment, by administering an effective amount of a compound of the present invention or a pharmaceutical composition comprising same, to the subject.

The compounds described herein are useful for treating cancer. In one embodiment, the cancer is brain cancer, glioma, sarcoma, breast cancer, lung cancer, non-small-cell lung cancer, mesothelioma, appendiceal cancer, genitourinary cancers, renal cell carcinoma, prostate cancer, bladder cancer, testicular cancer, penile cancer, cervical cancer, ovarian cancer, von Hippel Lindau disease, head and neck cancer, gastrointestinal cancer, hepatocellular carcinoma, gallbladder cancer, esophageal cancer, gastric cancer, colorectal cancer, pancreatic cancer, neuroendocrine tumors, thyroid tumor, pituitary tumor, adrenal tumor, hematological malignancy, or leukemia. In another embodiment, the cancer is B cell lymphoma. In another embodiment, the cancer is a melanoma.

In one embodiment the cancer is a lymphoma. In one embodiment, the lymphoma is a B cell lymphoma. In one embodiment, the B cell lymphoma is selected from the group consisting of a Hodgkin's B cell lymphoma and a non-Hodgkin's B cell lymphoma. In one embodiment, the B cell lymphoma is a non-Hodgkin's B cell lymphoma selected from the group consisting of DLBCL, follicular lymphoma, marginal zone lymphoma (MZL) or mucosa associated lymphatic tissue lymphoma (MALT), small cell lymphocytic lymphoma (overlaps with chronic lymphocytic leukemia) and mantle cell lymphoma. In one embodiment, the B cell lymphoma is a non-Hodgkin's B cell lymphoma selected from the group consisting of Burkitt's lymphoma, Primary mediastinal (thymic) large B-cell lymphoma, Lymphoplasmacytic lymphoma, which may manifest as Waldenstrom macroglobulinemia, Nodal marginal zone B cell lymphoma (NMZL), Splenic marginal zone lymphoma (SMZL), Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma, leg type (Primary cutaneous DLBCL, leg type), EBV positive diffuse large B-cell lymphoma of the elderly, Diffuse large B-cell lymphoma associated with inflammation, Intravascular large B-cell lymphoma, ALK-positive large B-cell lymphoma, and Plasmablastic lymphoma.

In one embodiment, the method is a method of treating a lymphoma using a combination therapy comprising a compound of the present invention and a chemotherapy regimen for the treatment of the lymphoma. In one embodiment, the chemotherapy regimen is the CHOP regimen. In another embodiment, the chemotherapy regimen is selected from COOP, CVP, EPOCH, Hyper-CVAD, ICE, R—CHOP, and R—CVP.

In the methods described here, the compounds can be administered by any suitable route, such as an oral, intravenous, or subcutaneous route.

EXAMPLES

The examples are illustrative only and do not limit the claimed invention.

Synthesis of 4,6-dichloro-2-(methylsulfonyl)pyrimidine (Intermediate I)

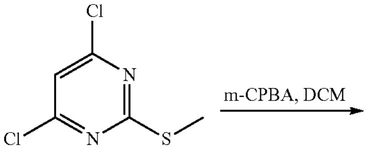

-continued

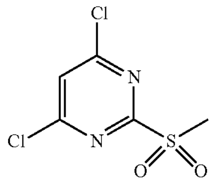

Intermediate I

To a solution of 4,6-dichloro-2-(methylthio)pyrimidine (9.75 g, 50 mmol) in dichloromethane (DCM) was slowly added meta-chloroperoxybenzoic acid (mCPBA) 22.4 g, 130 mmol) at 0° C. The reaction was allowed to warm to room temperature (RT) and stirred overnight. The mixture was quenched with an aqueous solution of 1M NaOH, extracted with DCM, washed with sat. aq. $NaHCO_3$ as well as brine, and the organic phase dried ($MgSO_4$), filtered and evaporated to give Intermediate I, 4,6-dichloro-2-(methylsulfonyl)pyrimidine, as a white solid (11.39 g). The product was used crude.

LC/MS (mobile phase 5-100% ACN in 3 min), Rt=0.94 min, $(M+H)^+$ 227

$^1$H NMR (300 MHz DMSO-d6): δ 8.30 (1H, s), 3.32 (3H, s)

Synthesis of 4,6-dichloro-2-(2-pyridin-2-yl)ethoxy) pyrimidine (Intermediate II)

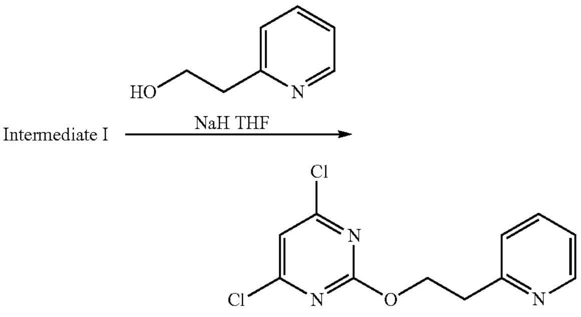

Intermediate II

To a solution of Intermediate I (11.3 g, 50 mmol) in tetrahydrofuran (THF) (60 ml) was added NaH (2.9 g, 72.5 mmol). The temperature was lowered to −78° C. and 2-(pyridin-2-yl)ethan-1-ol (6.5 g, 52.5 mmol) in THF (60 ml) was added dropwise. The reaction was stirred for 1 h at −78° C., and worked up by addition of water, followed by extraction with ethyl acetate (EtOAc), dried ($MgSO_4$), filtered and evaporated. The crude product was purified by silica gel chromatography using a gradient of hexane:EtOAc 9:1 to hexane:EtOAc 7:3. After evaporation of the correct fractions, 6.7 g of Intermediate II, 4,6-dichloro-2-(2-pyridin-2-yl)ethoxy)pyrimidine was obtained as a white solid.

LC/MS (mobile phase 5-100% ACN in 3 min), Rt=1.68 min, $(M+H)^+$ 270

$^1$H NMR (300 MHz DMSO-d6): δ 8.43 (1H, d), 7.66 (2H, m), 7.22 (1H, d), 7.15 (1H, m), 4.21 (2H, m), 3.29 (2H, m)

Synthesis of (3aR,6aR)-hexahydro-2H-furo[3,2-b] pyrrole (Intermediate III)

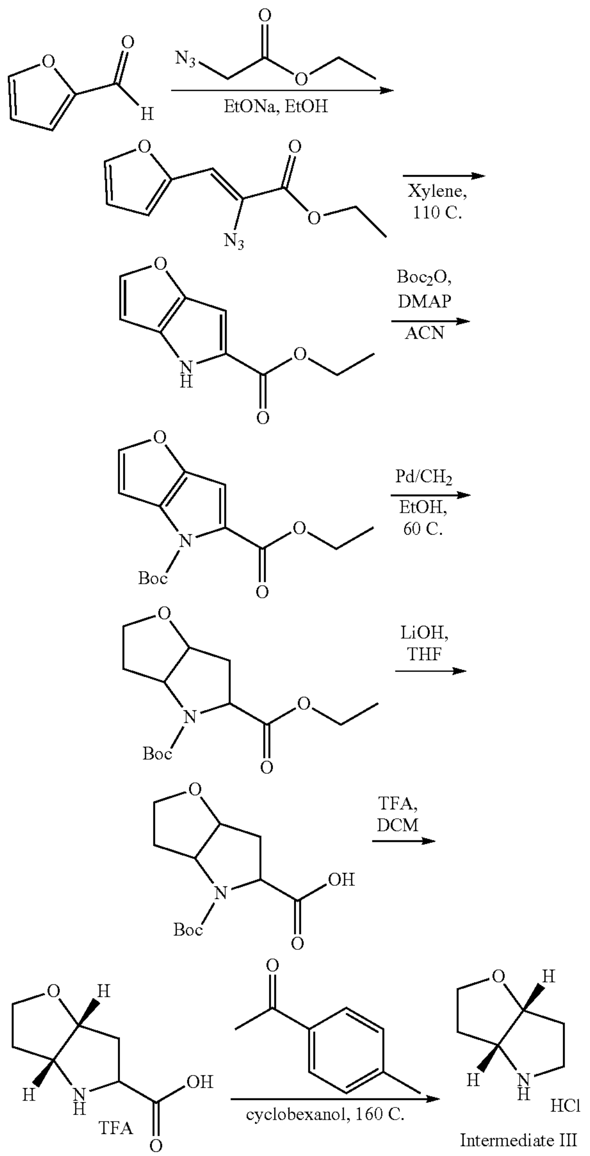

Intermediate III

To a solution of furan-2-carbaldehyde and ethyl 2-azidopropanoate in ethanol (EtOH) was added sodium ethoxide (1.1 eq) and the reaction heated at reflux overnight. Evaporated, redissolved in ethyl acetate, and washed with sat. aq. sodium bicarbonate, the organic phase dried ($MgSO_4$), filtered and evaporated. The crude product was redissolved in xylene and heated at 160° C. for 4 hours, then evaporated and purified by silica gel chromatography (EtOAc/hexane). Re-dissolved in ACN, 4-Dimethylaminopyridine (DMAP) added (0.1 eq) and $BOC_2O$ and stirred at rt for 5 h, worked up (as before), redissolved in EtOH and hydrogenated at 40 psi with Pd/C 105 for 2 h. Evaporated and treated with sat. aq. LiOH in THF at RT for 2 h. Evaporated and purified by LC/MS. The solid was redissolved in TFA/DCM 1:2 and stirred and rt for 2 h, evaporated, decarboxylated by heating, purified by LC/MS and covered to the HCl salt.

$^1$H NMR (300 MHz DMSO-d6): δ 83.68 (3H, m), 2.79 (3H, m), 2.01 (3H, m), 1.76 (2H, m)

Synthesis of 4-chloro-6-(3-(3-methoxyphenyl)-1H-pyrazol-1-yl)-2-(2-(pyridin-2-yl)ethoxy)pyrimidine (Intermediate IV)

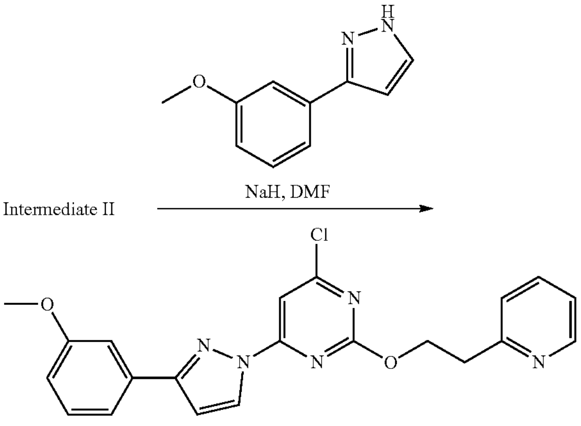

Intermediate IV

To a solution of Intermediate II, 4,6-dichloro-2-(2-(pyridin-2-yl)ethoxy)pyrimidine (269 mg, 1 mmol) in DMF (10 ml) was added 3-(3-methoxyphenyl)-1H-pyrazole (191 mg, 1.1 mmol) and NaH (19 mg, 1.2 mmol). The reaction was stirred at RT overnight, quenched with water, extracted with EtOAc, dried ($MgSO_4$), filtered, evaporated and purified by LCMS to give 4-chloro-6-(3-phenyl-1H-pyrazol-1-yl)-2-(2-(pyridin-2-yl)ethoxy)pyrimidine (Intermediate IV) (188 mg).

LC/MS $(M+H)^+$ 408

$^1$H NMR (300 MHz DMSO-d6): δ 8.43 (1H, m), 8.09 (1H, m), 7.76 (1H, s), 7.72 (2H, m), 7.47 (1H, m), 7.39 (1H, s), 7.18 (3H, m), 6.95 (1H, m), 4.25 (2H, m), 3.81 (3H, S), 3.30 (2H, m),

Synthesis of (3aR,6aR)-4-(6-chloro-2-((tetrahydrofuran-2-yl)methoxy)pyrimidin-4-yl)hexahydro-2H-furo[3,2-b]pyrrole (Intermediate V)

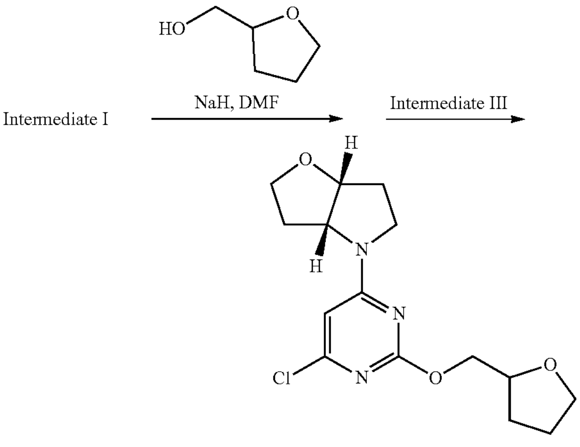

Intermediate V

To 2.8 g of Intermediate I (12.3 mml) was added NaH (770 mg, 32 mmol) and tetrahydrofuran-2-yl)methanol (1.81 g, 16 mmol) at 0° C. in THF (200 ml). The reaction was stirred at 2 h at RT, and Intermediate III (1.81 g, 16 mmol) added, and the reaction stirred overnight at RT. The reaction was worked up by quenching with water, evaporation, re-dissolved in ethyl acetate, washed (saturated aq. sodium bicarbonate), dried ($MgSO_4$), filtered and evaporated. The crude mixture was purified by silica gel chromatography (hexane/ethyl acetate) to give 2.2 g of Intermediate V.

LC/MS (mobile phase 5-100% ACN in 5 min), Rt=3.36 min, $(M+H)^+$ 326

$^1$H NMR (300 MHz $CDCl_3$): δ 7.29 (s, 1H), 4.49 (m, 5H), 3.37 (m, 6H), 2.24 (m, 2H), 2.13 (m, 1H), 1.90 (m, 5H)

Synthesis of 4-(6-chloro-2-((tetrahydrofuran-2-yl)methoxy)pyrimidin-4-yl)morpholine (Intermediate VI)

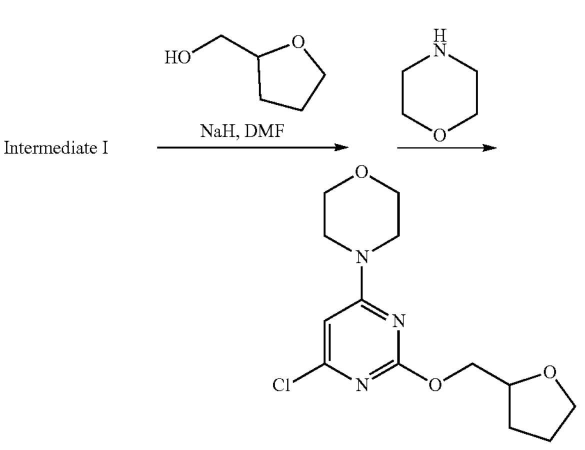

Intermediate VI

Intermediate VI was prepared by a method analogous to Intermediate V, except morpholine was added instead of Intermediate III.

LC/MS (mobile phase 5-100% ACN in 4 min), Rt=2.22 min, $(M+H)^+$ 300

$^1$H NMR (300 MHz DMSO-d6): δ 6.62 (s, 1H), 4.19 (m, 1H), 4.14 (m, 1H), 3.77 (m, 1H), 3.62 (m, 9H), 1.97 (m, 1H), 1.85 (m, 2H), 1.62 (m, 1H)

Synthesis of 4-chloro-2-((tetrahydrofuran-2-yl)methoxy)-6-(3-(m-tolyl)-1H-pyrazol-1-yl)pyrimidine (Intermediate VII)

Intermediate VII

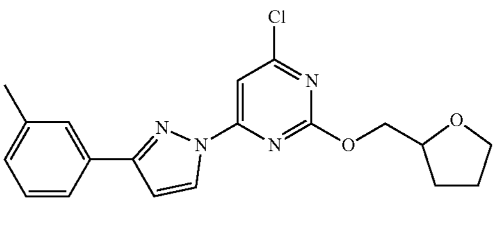

Intermediate VII was prepared by a method analogous to Intermediate IV, except tetrahydrofuran-2-yl)methanol was added in place of 2-(pyridin-2-yl)ethan-1-ol to generate the equivalent of Intermediate II and 5-(m-tolyl)-1H-pyrazole was added in place of 3-(3-methoxyphenyl)-1H-pyrazole to generate Intermediate VII.

LC/MS (mobile phase 5-100% ACN in 4 min), Rt=3.52 min, $(M+H)^+$ 371

$^1$H NMR (300 MHz DMSO-d6): δ 8.75 (s, 1H), 7.77 (s, 1H), 7.81 (d, 1H), 7.68 (s, 1H), 7.39 (m, 1H), 7.27 (m, 1H), 7.21 (s, 1H), 4.40 (m, 2H), 2.16 (m, 1H), 3.83 (m, 1H0, 3.72 (m, 1H), 2.40 (s, 3H), 2.06 (m, 1H), 1.88 (m, 2H), 1.72 (m, 1H)

Synthesis of 4-chloro-2-(2-(tetrahydrofuran-2-yl)ethyl)-6-(3-(m-tolyl)-1H-pyrazol-1-yl)pyrimidine (Intermediate VIII)

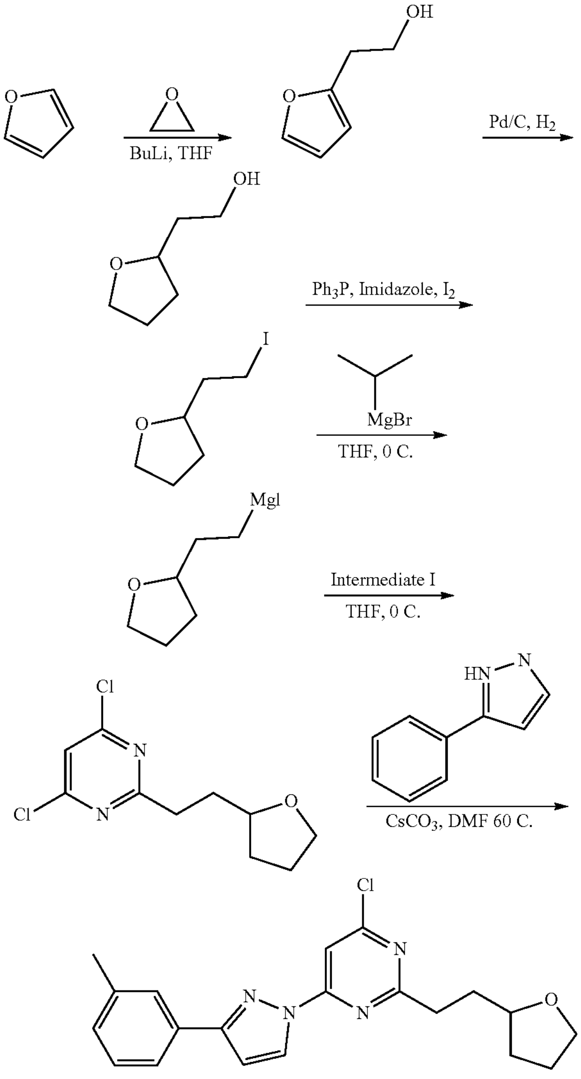

Intermediate VIII

Intermediate VIII was prepared by the scheme shown above.

LC/MS (mobile phase 5-100% ACN in 5 min), Rt=4.32 min, $(M+H)^+$ 369

$^1$H NMR (300 MHz DMSO-d6): δ 8.72 (s, 1H), 7.89 (m, 2H), 7.81 (m, 1H), 7.39 (m, 1H), 7.26 (m, 1H), 7.20 (s, 1H), 3.82 (m, 1H), 3.75 (m, 1H), 3.60 (m, 1H), 2.90 (m, 2H), 2.40 (s, 3H), 2.00 (m, 3H), 1.82 (m, 2H), 1.49 (m, 1H)

Example 1: Synthesis of 3aR,6aR)-4-(6-(3-(3-methoxyphenyl)-1H-pyrazol-1-yl)-2-((tetrahydrofuran-2-yl)methoxy)pyrimidin-4-yl)hexahydro-2H-furo[3,2-b]pyrrole (Compound 1)

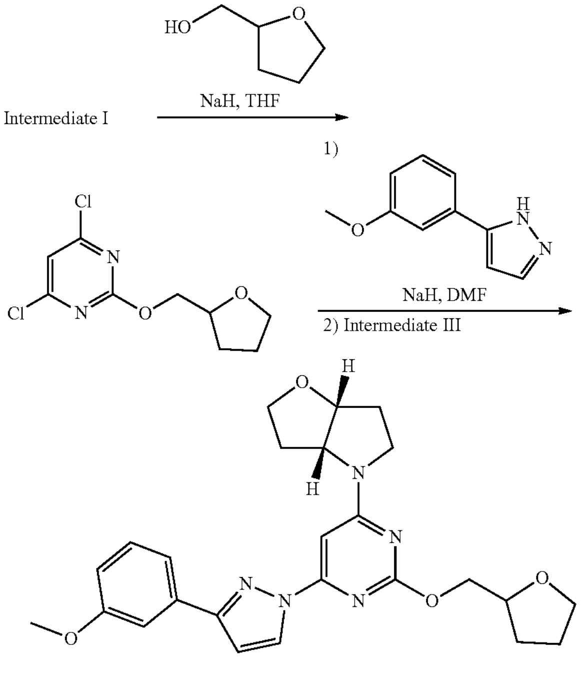

1

To a solution of Intermediate I, 4,6-dichloro-2-(methylsulfonyl)pyrimidine (113 mg, 0.5 mmol) in THF (5 ml), was added NaH (14 mg, 0.64 mmol) and the solution cooled to −78° C. Tetrahydrofuran-2-yl)methanol (51 mg, 0.48 mmol) was added dropwise as a solution in THF (1 ml), and the solution stirred for 1 h at −78° C., then quenched with water, extracted with EtOAc, dried (MgSO4), filtered, evaporated and purified by silica gel chromatography (hexane/EtOAc) to give 16 mg of 4,6-dichloro-2-((tetrahydrofuran-2-yl)methoxy)pyrimidine. This was dissolved in dimethylformamide (DMF) (1 ml), NaH (4 mg, 0.18 mmol) was added, followed by 5-(3-methoxyphenyl)-1H-pyrazole (16 mg, 0.09 mmol), and the reaction mixture stirred for 1 h at RT. Intermediate III (44 mg) was added, and the reaction stirred overnight at RT, then quenched with water, extracted with EtOAc, dried ($MgSO_4$), filtered, evaporated and purified by LC/MS to give 8 mg of (3aR,6aR)-4-(6-(3-(3-methoxyphenyl)-1H-pyrazol-1-yl)-2-((tetrahydrofuran-2-yl)methoxy)pyrimidin-4-yl)hexahydro-2H-furo[3,2-b]pyrrole Compound 1.

LC/MS (mobile phase 5-100% ACN in 5 min), Rt=3.91 min, $(M+H)^+$ 464

Example 2: Synthesis of 4-(6-(3-(3-methoxyphenyl)-1H-pyrazol-1-yl)-2-((tetrahydrofuran-2-yl)methoxy)pyrimidin-4-yl)morpholine (Compound 2)

2

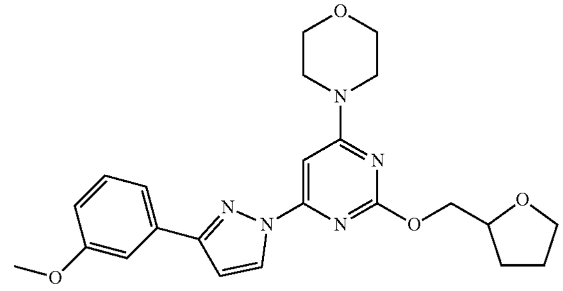

To a solution of Intermediate I, 4,6-dichloro-2-(methylsulfonyl)pyrimidine (113 mg, 0.5 mmol) in THF (5 ml), was added NaH (14 mg, 0.64 mmol) and the solution cooled to −78° C. Tetrahydrofuran-2-yl)methanol (51 mg, 0.48 mmol) was added dropwise as a solution in THF (1 ml), and the solution stirred for 1 h at −78° C., then quenched with water, extracted with EtOAc, dried ($MgSO_4$), filtered, evaporated and purified by silica gel chromatography (hexane/EtOAc) to give 23 mg of 4,6-dichloro-2-((tetrahydrofuran-2-yl)methoxy)pyrimidine. This was dissolved in DMF (3 ml), NaH (6 mg) was added, followed by 5-(3-methoxyphenyl)-1H-pyrazole (16 mg) and the reaction mixture stirred for 1 h at RT. Morpholine (9 ul) was added, and the reaction stirred overnight at rt, then quenched with water, extracted with EtOAc, dried ($MgSO_4$), filtered, evaporated and purified by LC/MS to give 6 mg of 4-(6-(3-(3-methoxyphenyl)-1H-pyrazol-1-yl)-2-((tetrahydrofuran-2-yl)methoxy)pyrimidin-4-yl)morpholine, Compound 2.

LC/MS (mobile phase 5-100% ACN in 5 min), Rt=3.90 min, $(M+H)^+$ 438

Example 3: Synthesis of 4-(6-(3-phenyl-1H-pyrazol-1-yl)-2-(2-(tetrahydro-2H-pyran-4-yl)ethoxy)pyrimidin-4-yl)morpholine (Compound 3)

3

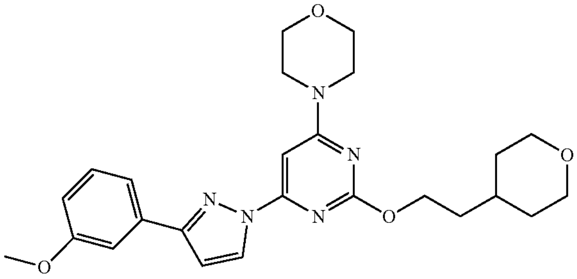

To a solution of Intermediate I, 4,6-dichloro-2-(methylsulfonyl)pyrimidine (113 mg, 0.5 mmol) in THF (5 ml), was added NaH (14 mg, 0.64 mmol) and the solution cooled to −78° C. 2-(tetrahydro-2H-pyran-4-yl)ethan-1-ol (65 mg) was added dropwise as a solution in THF (1 ml), and the solution stirred for 1 h at −78° C., then quenched with water, extracted with EtOAc, dried ($MgSO_4$), filtered, evaporated and purified by silica gel chromatography (hexane/EtOAc) to give 65 mg of 4-(2-(3,5-dichlorophenoxy)ethyl)tetrahydro-2H-pyran. This was dissolved in DMF (3 ml), NaH (9 mg) was added, followed by 5-(3-methoxyphenyl)-1H-pyrazole (41 mg) and the reaction mixture stirred for 1 h at RT. Morpholine (21 ul) was added, and the reaction stirred overnight at rt, then quenched with water, extracted with EtOAc, dried ($MgSO_4$), filtered, evaporated and purified by LC/MS to give 9 mg of 4-(6-(3-(3-methoxyphenyl)-1H-pyrazol-1-yl)-2-(2-(tetrahydro-2H-pyran-4-yl)ethoxy)pyrimidin-4-yl)morpholine, Compound 3.

LC/MS (mobile phase 5-100% ACN in 5 min), Rt=4.14 min, $(M+H)^+$ 466

Example 4: Synthesis of (3aR,6aR)-4-(6-(3-phenyl-1H-pyrazol-1-yl)-2-(2-(pyridin-2-yl)ethoxy)pyrimidin-4-yl)hexahydro-2H-furo[3,2-b]pyrrole (Compound 4)

4

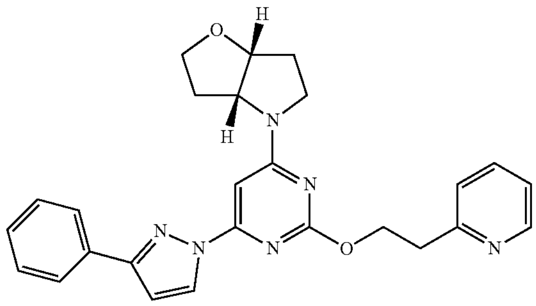

Compound 4 was prepared by a method analogous to that for Compound 1, except Intermediate III was used in place of morpholine and 5-phenyl-1H-pyrazole was used in place of 5-(3-methoxyphenyl)-1H-pyrazole.

LC/MS (mobile phase 5-100% ACN in 5 min), Rt=3.16 min, $(M+H)^+$ 455

Example 5: Synthesis of 2-((4-((3aR,6aR)-hexahydro-4H-furo[3,2-b]pyrrol-4-yl)-6-(3-(3-methoxyphenyl)-1H-pyrazol-1-yl)pyrimidin-2-yl)oxy)ethan-1-ol (Compound 5)

5

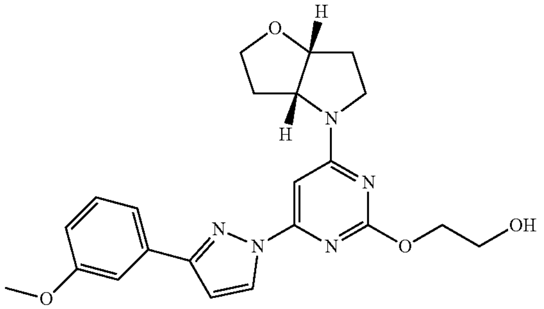

Compound 5 was prepared by a method analogous to that for Compound 1, except 2-(tert-butoxy)ethan-1-ol was added instead of tetrahydrofuran-2-yl)methanol, and the end product was treated with trifluoroacetic acid (TFA)/DCM 1:2 for 1 h at RT and evaporated prior to purification by LC/MS.

LC/MS (mobile phase 5-100% ACN in 5 min), Rt=3.16 min, $(M+H)^+$ 424

Example 6: Synthesis of (3aR,6aR)-4-(6-(3-(3-methoxyphenyl)-1H-pyrazol-1-yl)-2-(2-(4-methylthiazol-5-yl)ethoxy)pyrimidin-4-yl)hexahydro-2H-furo[3,2-b]pyrrole (Compound 6)

6

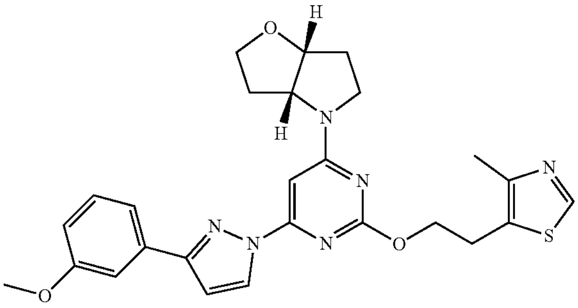

Compound 6 was prepared by a method analogous to that for Compound 1, except 2-(4-methylthiazol-5-yl)ethan-1-ol was added instead of tetrahydrofuran-2-yl)methanol.

LC/MS (mobile phase 5-100% ACN in 5 min), Rt=3.60 min, $(M+H)^+$ 505

Example 7: Synthesis of 4-(6-(3-(3-methoxyphenyl)-1H-pyrazol-1-yl)-2-(2-(4-methylthiazol-5-yl)ethoxy)pyrimidin-4-yl)morpholine (Compound 7)

7

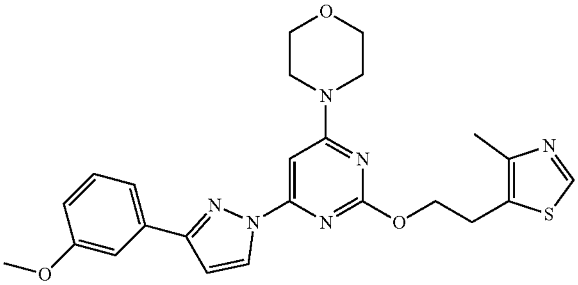

Compound 7 was prepared by a method analogous to that for Compound 6, except morpholine was used in place of Intermediate III.

LC/MS (mobile phase 5-100% ACN in 5 min), Rt=3.56 min, $(M+H)^+$ 479

Example 8: Synthesis of 4-((4-((3aR,6aR)-hexahydro-4H-furo[3,2-b]pyrrol-4-yl)-6-(3-(3-methoxyphenyl)-1H-pyrazol-1-yl)pyrimidin-2-yl)oxy)butane-1,2-diol (Compound 8)

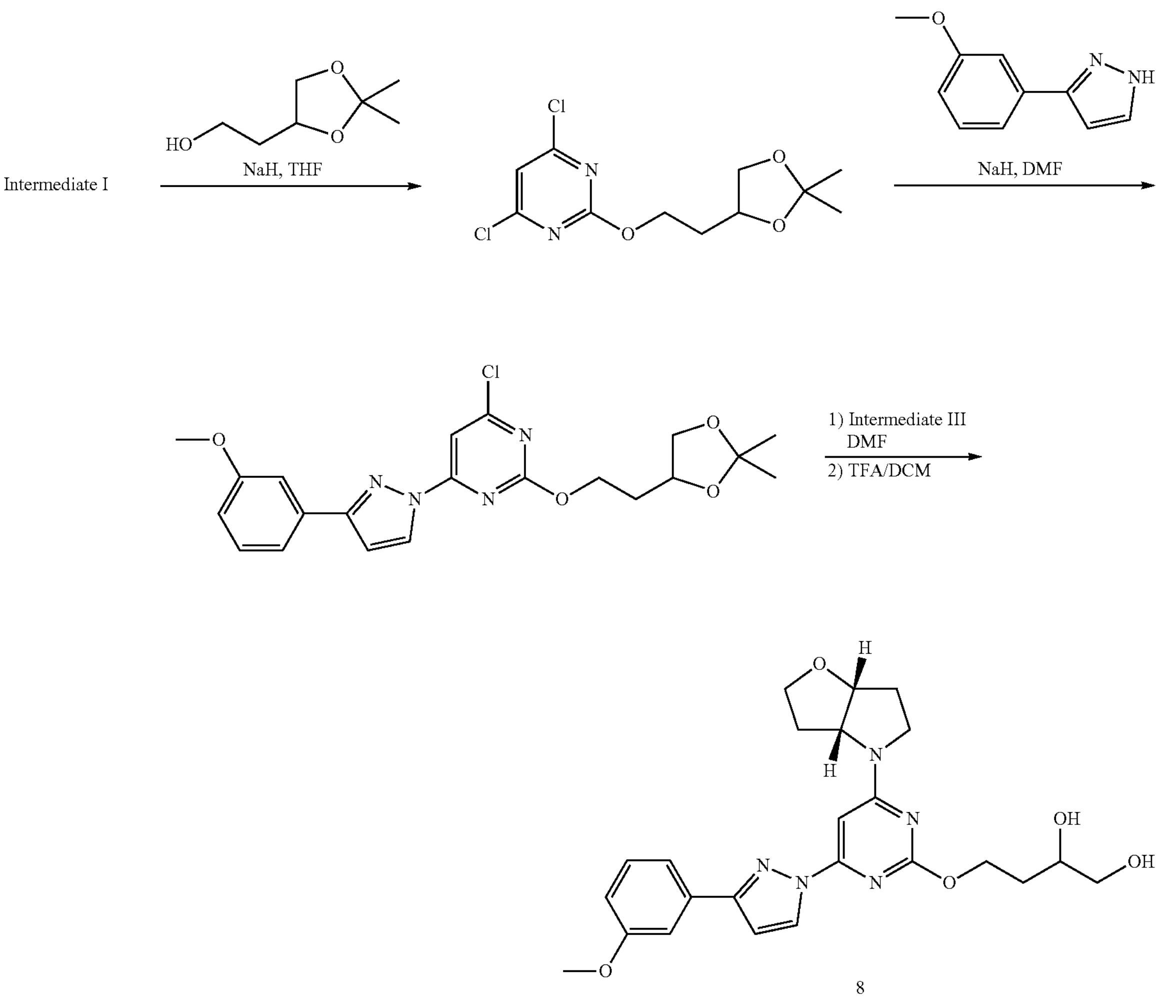

8

To a solution of Intermediate I, (113 mg, 0.5 mmol) in THF (5 ml) was added NaH (18.4 mg, 0.8 mmol) and the temperature lowered to −78° C. 2-(2,2-dimethyl-1,3-dioxolan-4-yl)ethan-1-ol 71 ul, 0.5 mmol) in THF (1 ml) was added dropwise and the reaction stirred at 1 h at −78° C., worked up by quenching with water, extraction with EtOAc, dried ($MgSO_4$), filtered and evaporated. Dissolved in THF (3 ml), 3-(3-methoxyphenyl)-1H-pyrazole (18 mg) and NaH (7.5 mg) were added, and the reaction was stirred for 1 h at rt. Intermediate III (35 mg) was added, and the reaction stirred overnight at rt. Quenched with water, evaporated and purified on HPLC, then treated with TFA/DCM 1:2 (0.5 ml), evaporated and purified by LC/MS to give 6 mg of 4-(3-((3aR,6aR)-hexahydro-4H-furo[3,2-b]pyrrol-4-yl)-5-(3-(3-methoxyphenyl)-1H-pyrazol-1-yl)phenoxy)butane-1,2-diol (Compound 8).

LC/MS (mobile phase 5-100% ACN in 5 min), Rt=3.20 min, $(M+H)^+$ 468

Example 9: Synthesis of 4-((4-(3-(3-methoxyphenyl)-1H-pyrazol-1-yl)-6-morpholinopyrimidin-2-yl)oxy)butane-1,2-diol (Compound 9)

9

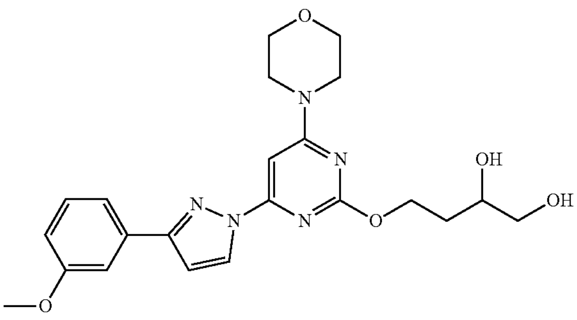

Compound 9 was prepared by a method analogous to that for Compound 8, except morpholine was used in place of Intermediate III.

LC/MS (mobile phase 5-100% ACN in 5 min), Rt=3.18 min, $(M+H)^+$ 442

Example 10: Synthesis 4-(6-(4-phenyl-1H-imidazol-1-yl)-2-(2-(pyridin-2-yl)ethoxy)pyrimidin-4-yl)morpholine (Compound 10)

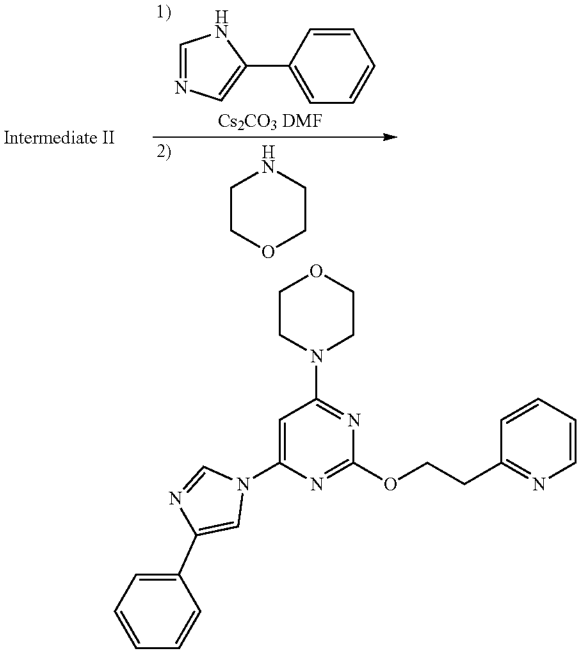

10

To a solution of Intermediate II (27 mg, 0.1 mmol) in DMF (1 ml) was added $Cs_2CO_3$ (65 mg, 0.2 mmol), followed by 5-phenyl-1H-imidazole (5 mg, 0.1 mmol). The reaction was stirred for 70 min at RT, and morpholine (30 ul) was added and the reaction stirred for 60 min. The mixture was evaporated and purified by LC/MS to give 18 mg of 4-(6-(4-phenyl-1H-imidazol-1-yl)-2-(2-(pyridin-2-yl)ethoxy)pyrimidin-4-yl)morpholine (Compound 10).

LC/MS (mobile phase 5-100% ACN in 5 min), Rt=3.18 min, $(M+H)^+$ 429

Example 11: Synthesis of (3aR,6aR)-4-(2-((tetrahydrofuran-2-yl)methoxy)-6-(4-(m-tolyl)thiazol-2-yl)pyrimidin-4-yl)hexahydro-2H-furo[3,2-b]pyrrole (Compound 11)

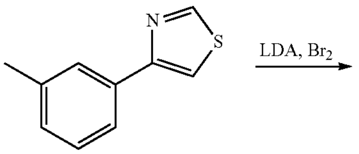

-continued

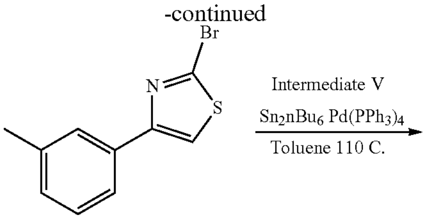

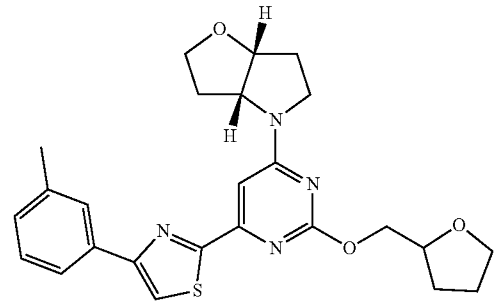

11

400 mg of 4-(m-tolyl)thiazole was treated with LDA (1.1 eq) and bromine (1.5 eq) to give 2-bromo-4-(m-tolyl)thiazole. 2-bromo-4-(m-tolyl)thiazole was further converted to (3aR,6aR)-4-(2-((tetrahydrofuran-2-yl)methoxy)-6-(4-(m-tolyl)thiazol-2-yl)pyrimidin-4-yl)hexahydro-2H-furo[3,2-b]pyrrole (Compound 11) as illustrated in the scheme above. 4 mg of product was obtained.

LC/MS (mobile phase 5-100% ACN in 5 min), Rt=3.78 min, $(M+H)^+$ 465

Example 12: Synthesis of 4-(2-((tetrahydrofuran-2-yl)methoxy)-6-(4-(m-tolyl)thiazol-2-yl)pyrimidin-4-yl)morpholine (Compound 12)

12

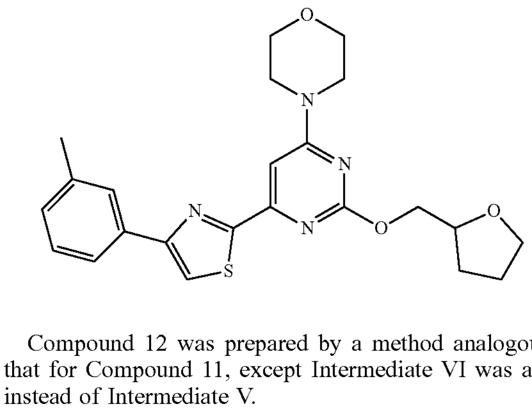

Compound 12 was prepared by a method analogous to that for Compound 11, except Intermediate VI was added instead of Intermediate V.

LC/MS (mobile phase 5-100% ACN in 3 min), Rt=2.18 min, $(M+H)^+$ 439

$^1H$ NMR (300 MHz MeOD): δ 8.26 (s, 1H), 7.86 (m, 2H), 7.38 (m, 2H), 7.24 (s, 1H), 3.35 (m, 3H), 3.94 (m, 1H), 3.80 (m, 9H), 2.47 (s, 3H), 2.01 (m, 4H)

Example 13: Synthesis of 4-(2-((tetrahydrofuran-2-yl)methoxy)-6-(1-(m-tolyl)-1H-pyrazol-3-yl)pyrimidin-4-yl)morpholine (Compound 13)

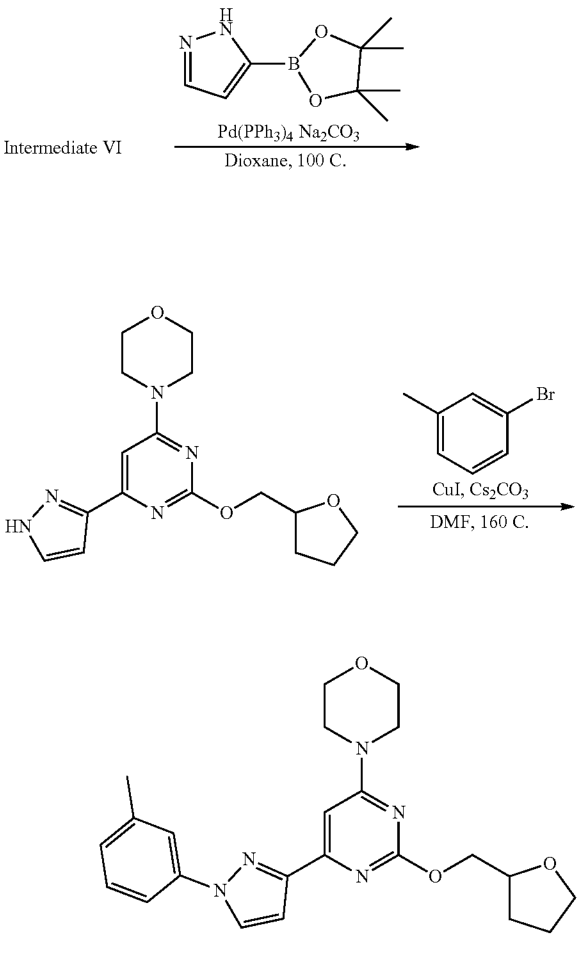

13

To 200 mg of Intermediate VI in degassed dioxane (10 ml) was added $Na_2CO_3$ (1.5 eq), $Pd(PPh_3)_4$ (0.1 eq) and 5-(4,4,5,5-tetramethyl-1,3,2-dioxaborolan-2-yl)-1H-pyrazole (1.3 eq). The reaction was stirred at 100° C. for 2 h under argon. The mixture was evaporated, re-dissolved in EtOAc, washed (saturated aq. sodium bicarbonate), dried ($MgSO_4$), filtered and evaporated. Re-dissolved in DMF (10 ml), 3-bromotoluene (30 eq), CuI (1 eq) and $Cs_2CO_3$ (1.1 eq) were added, and the mixture heated at 160° C. for 4 h. The mixture was evaporated, re-dissolved in EtOAc, washed (saturated aq. bicarbonate), dried ($MgSO_4$), filtered, evaporated, and purified by LC/MS to give 147 mg of Compound 13.

LC/MS (mobile phase 5-100% ACN in 3 min), Rt=1.52 min, $(M+H)^+$ 422

$^1H$ NMR (300 MHz MeOD): δ 8.28 (s, 1H), 7.71 (s, 1H), 7.65 (m, 1H), 7.39 (m, 1H), 7.21 (d, 1H), 7.11 (m, 2H), 4.39 (m, 3H), 3.93 (m, 1H), 3.78 (m, 9H), 2.49 (s, 3H), 2.00 (m, 4H)

Example 14: Synthesis of 4-(2-((tetrahydrofuran-2-yl)methoxy)-6-(3-(m-tolyl)-1H-pyrazol-1-yl)pyrimidin-4-yl)-1,4-oxazepane (Compound 14)

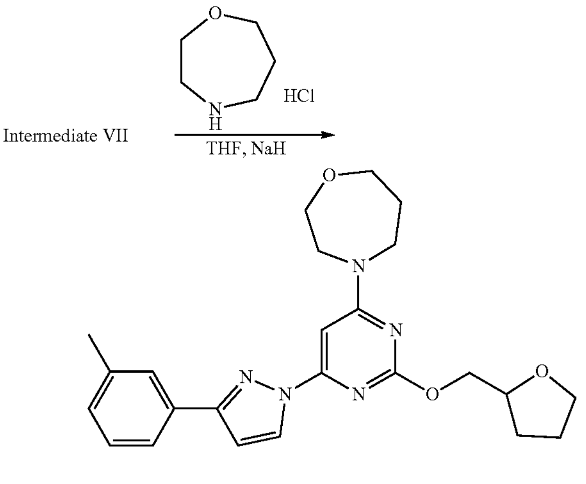

14

To Intermediate VII in THF was added NaH (3.1 eq.) and 1,4-oxepane (3 eq). The mixture was stirred at RT for 2 h. Purified by LC/MS to give Compound 14.

LC/MS (mobile phase 5-100% ACN in 5 min), Rt=3.19 min, $(M+H)^+$ 436

$^1H$ NMR (300 MHz $CDCl_3$): δ 8.60 (s, 1H), 7.79 (s, 1H), 7.73 (m, 1H), 7.35 (m, 1H), 7.20 (m, 1H) 6.88 (s, 1H), 6.76 (s, 1H), 4.43 (m, 1H), 4.34 (m, 2H), 3.90 (m, 7H), 3.77 (m, 3H), 2.46 (s, 3H), 2.12 (m, 3H), 1.99 (m, 2H), 1.83 (m, 1H)

Example 15: Synthesis of 4-(3-methoxypyrrolidin-1-yl)-2-((tetrahydrofuran-2-yl)methoxy)-6-(3-(m-tolyl)-1H-pyrazol-1-yl)pyrimidine (Compound 15)

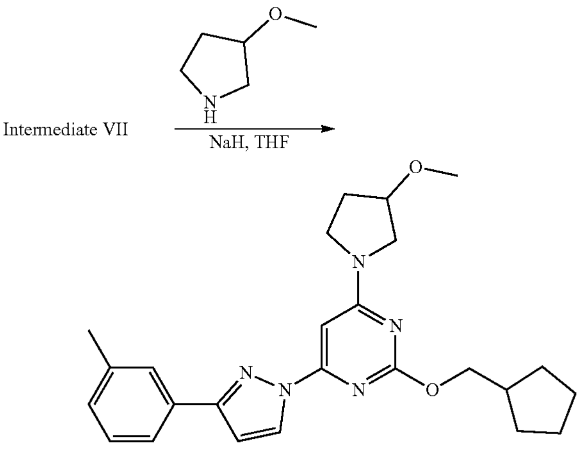

15

Compound 15 was prepared by a method analogous to that for Compound 14.

LC/MS (mobile phase 5-100% ACN in 5 min), Rt=3.71 min, $(M+H)^+$ 436

$^1H$ NMR (300 MHz $CDCl_3$): δ 8.58 (s, 1H), 7.78 (s, 1H), 7.72 (m, 1H), 7.34 (m, 1H), 7.20 (m, 1H), 6.71 (d, 2H), 4.48 (m, 1H), 4.35 (m, 2H), 4.11 (m, 1H), 3.97 (m, 3H), 3.69 (m, 3H), 3.41 (s, 3H), 2.43 (s, 3H), 2.26 (m, 3H), 2.00 (m, 2H), 1.83 (m, 1H)

Example 16: Synthesis of (3aR,6aR)-4-(6-(3-(3-methoxyphenyl)-1H-pyrazol-1-yl)-2-(2-(pyridin-2-yl)ethoxy)pyrimidin-4-yl)hexahydro-2H-furo[3,2-b]pyrrole (Compound 16)

16

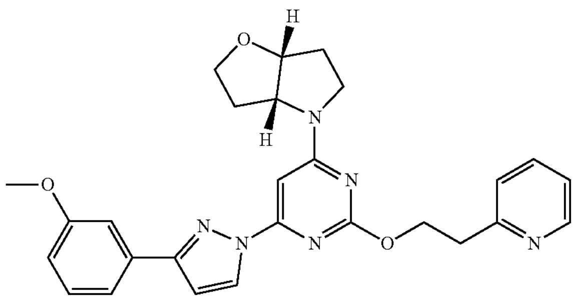

Compound 16 was prepared by a method analogous to that for Compound 4, except 5-(3-methoxyphenyl)-1H-pyrazole was added instead of 5-phenyl-1H-pyrazole.

LC/MS (mobile phase 5-100% ACN in 5 min), Rt=3.89 min, $(M+H)^+$ 485

Example 17: Synthesis of 2-((tetrahydrofuran-2-yl)methoxy)-4-(tetrahydrofuran-3-yl)-6-(3-(m-tolyl)-1H-pyrazol-1-yl)pyrimidine (Compound 17)

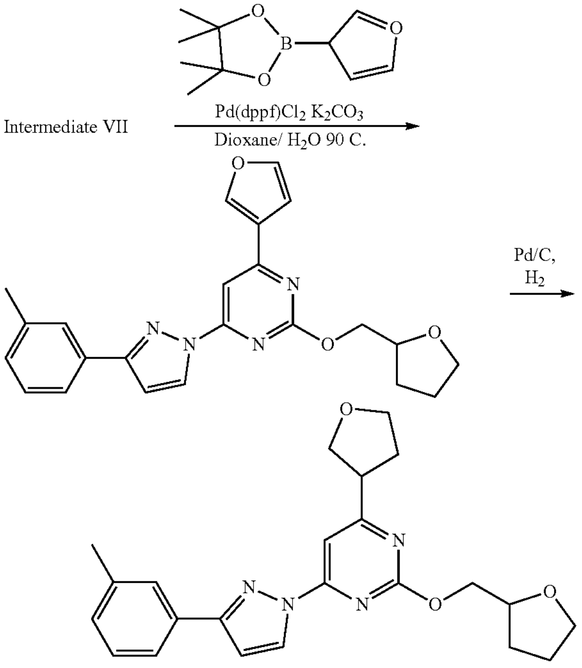

17

To 100 mg of Intermediate VII in degassed dioxane/water 9:1 was added 2-(furan-3-yl)-4,4,5,5-tetramethyl-1,3,2-dioxaborolane (1.2 eq), $K_2CO_3$ (1.1 eq) and $Pd(dppf)Cl_2$ (0.3 eq) and the mixture was heated under argon at 90° C. overnight. The mixture was evaporated, re-dissolved in EtOAc and saturated aq. bicarbonate, the layers separated, washed with bicarbonate, dried ($MgSO_4$), filtered, and evaporated. Re-dissolved in EtOH, Pd/C added and hydrogenated for 4 h at RT. Purified by LC/MS.

LC/MS (mobile phase 5-100% ACN in 3 min), Rt=2.34 min, $(M+H)^+$ 407

$^1H$ NMR (300 MHz $CDCl_3$): δ 8.62 (s, 1H), 7.79 (s, 1H), 7.73 (d, 1H), 7.61 (s, 1H), 7.35 (m, 1H), 7.24 (m, 1H), 6.81 (s, 1H), 4.45 (m, 3H), 4.22 (m, 1H), 4.12 (m, 1H), 3.85 (m, 1H), 3.61 (m, 1H), 3.39 (m, 2H), 2.49 (s, 3H), 2.11 (m, 3H), 1.83 (m, 1H)

Example 18: Synthesis of 4-((2-methoxyethyl)thio)-2-((tetrahydrofuran-2-yl)methoxy)-6-(3-(m-tolyl)-1H-pyrazol-1-yl)pyrimidine (Compound 18)

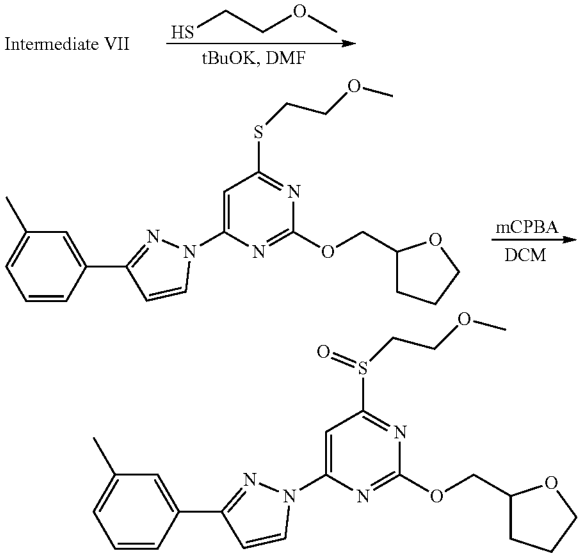

18

To 60 mg of Intermediate VII in DMF (4 ml) was added tBuOK (1.1 eq) and 2-methoxyethane-1-thiol (1.2 eq) and the reaction stirred at RT overnight. The mixture was evaporated, re-dissolved in EtOAc, washed with sat aq. $NaHCO_3$, dried ($MgSO_4$), filtered and evaporated. Re-dissolved in DCM (4 ml) and 1.5 eq of mCPBA added, stirred at RT for 4 h, worked up as described for the last step and purified by LC/MS to give Compound 18.

LC/MS (mobile phase 5-100% ACN in 3 min), Rt=1.92 min, $(M+H)^+$ 443

$^1H$ NMR (300 MHz $CDCl_3$): δ 8.61 (1H, s), 8.33 (1H, s), 7.82 (1H, s), 7.71 (1H, m), 7.35 (1H, m), 7.24 (1H, m), 6.86 (1H, s), 4.42 (3H, m), 3.90 (4H, m), 3.47 (4H, m), 3.19 (1H, m), 2.48 (3H, s), 2.08 (3H, m), 1.82 (1H, m)

Example 19: Synthesis of (3aR,6aR)-4-(6-(3-phenyl-1H-pyrazol-1-yl)-2-(2-(pyrimidin-2-yl)ethyl)pyrimidin-4-yl)hexahydro-2H-furo[3,2-b]pyrrole (Compound 19)

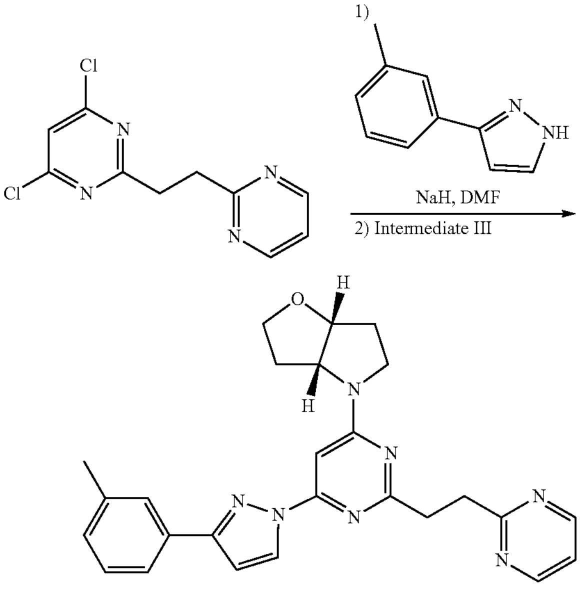

19

To 4,6-dichloro-2-(2-(pyrimidin-2-yl)ethyl)pyrimidine (22 mg, 0.09 mmol) in DMF (4 ml) was added 3-(m-tolyl)-1H-pyrazole (47 mg, 0.3 mmol) and NaH (50 mg). The mixture was shaken for 2 h at RT and (3aR,6aR)-hexahydro-412-furo[3,2-b]pyrrole (27 mg, 0.09 mmol) added. The reaction was heated to 80° C. for 4 h and purified by LC/MS to give 7 mg of (3aR,6aR)-4-(6-(3-phenyl-1H-pyrazol-1-yl)-2-(2-(pyrimidin-2-yl)ethyl)pyrimidin-4-yl)hexahydro-2H-furo[3,2-b]pyrrole (Compound 19).

LC/MS (mobile phase 5-100% ACN in 5 min), Rt=4.02 min, $(M+H)^+$ 454

Example 20: Synthesis of (4-(2-(2-(tetrahydrofuran-2-yl)ethyl)-6-(3-(m-tolyl)-1H-pyrazol-1-yl)pyrimidin-4-yl)morpholin-3-yl)methanol (Compound 20)

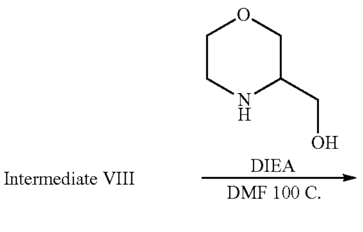

-continued

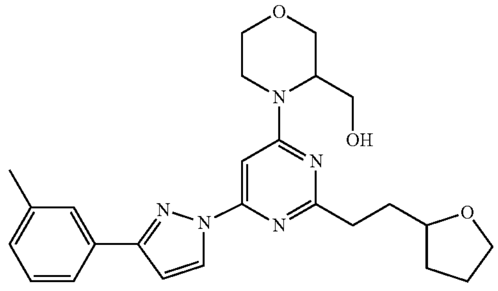

20

To 60 mg of Intermediate VIII in DMF (3 ml) was added $Cs_2CO_3$ (3 eq) and morpholin-3-ylmethanol (3 eq). The reaction was heated at 100 C for 6 h, evaporated and purified by LC/MS to give 22 mg of Compound 20.

LC/MS (mobile phase 5-100% ACN in 3 min), Rt=2.03 min, $(M+H)^+$ 450

$^1H$ NMR (300 MHz DMSO-d6): δ 8.62 (1H, s), 7.80 (2H, m), 7.36 (1H, m), 7.22 (1H, m), 7.03 (2H, m), 4.99 (1H, m), 4.29 (1H, b), 4.08 (1H, d), 3.95 (1H, m), 3.79 (3H, m), 3.55 (4H, m), 3.76 (2H, m), 2.40 (3H, s), 1.98 (3H, m), 1.82 (2H, m), 1.46 (1H, m)

Biological Activity

The activity of Compounds 1-20 was measured using a PIKFYVE assay (luciferase ADP-Glo kinase assay available from Promega Corp. of Madison, WI). The activity for each compound is provided in Table 1 below ("A" refers to an $IC_{50}$ of less than 5 nM, "B" refers to an $IC_{50}$ of 5-100 nM, "C" refers to an $IC_{50}$ of 101-1,000 nM, and "D" refers to an $IC_{50}$ of 1,001-10,000 nM).

TABLE 1

| Compound | PIKFYVE Activity ($IC_{50}$ in nM) |
|---|---|
| Compound 1 | B |
| Compound 2 | A |
| Compound 3 | A |
| Compound 4 | C |
| Compound 5 | C |
| Compound 6 | B |
| Compound 7 | A |
| Compound 8 | B |
| Compound 9 | A |
| Compound 10 | D |
| Compound 11 | C |
| Compound 12 | B |
| Compound 13 | B |
| Compound 14 | C |
| Compound 15 | D |
| Compound 16 | C |
| Compound 17 | B |
| Compound 18 | D |
| Compound 19 | B |
| Compound 20 | B |

All references cited herein are incorporated by reference.

The invention claimed is:

1. A compound of the formula (I)

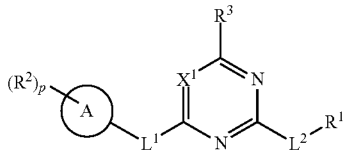

(I)

or a pharmaceutically acceptable salt thereof, wherein $R^1$ is hydroxy, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

$R^2$ is substituted phenyl;

$R^3$ is selected from:

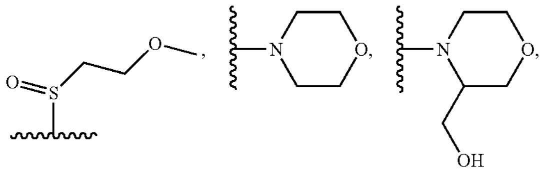

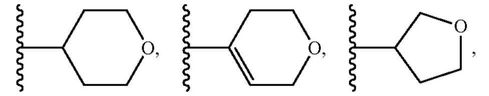

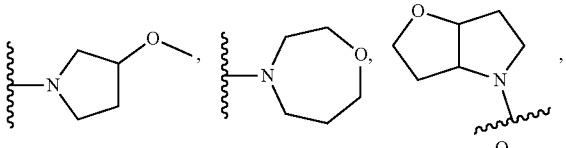

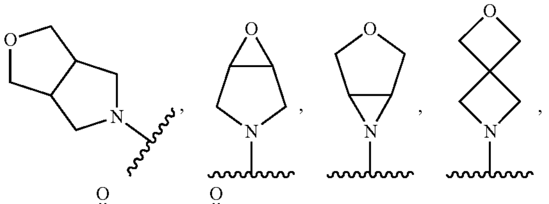

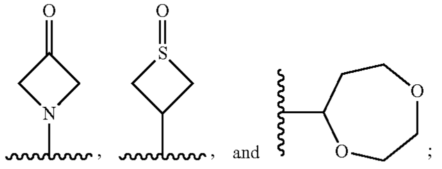

Ring A is (i) 5 or 6-membered heteroaryl having at least one nitrogen or oxygen ring atom, or (ii) phenyl;

$L^1$ is absent, $C_1$-$C_2$ alkylene, —O—, —S—, —C(O)—, —NHC(O)—, or —C(O)NH—;

$L^2$ is —O—$(CR^aR^b)_m$—, $NR^c$—$(CR^aR^b)_m$—, or —S—$(CR^aR^b)_m$—;

$X^1$ is CH, N, or $CR^c$;

each occurrence of $R^a$ and $R^b$ are independently hydrogen, hydroxy, hydroxy($C_{1-4}$)alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —$C(O)R^d$, —$C(S)R^d$, —$OC(O)R^d$, —SC(O)$R^d$, $OC(S)R^d$, $SC(S)R^d$, —$NR^cC(O)R^d$, —$NR^cC(S)R^d$, —$SO_2R^c$, —$S(O)R^c$, —$NR^cSO_2R^d$, —$OS(O)_2R^d$, —$OP(O)R^dR^e$, or —$P(O)R^dR^e$;

$R^c$ is hydrogen or $C_{1-6}$ alkyl;

each occurrence of $R^d$ and $R^e$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

m is 1-4; and p is 1.

2. The compound of claim 1, wherein $R^3$ is selected from

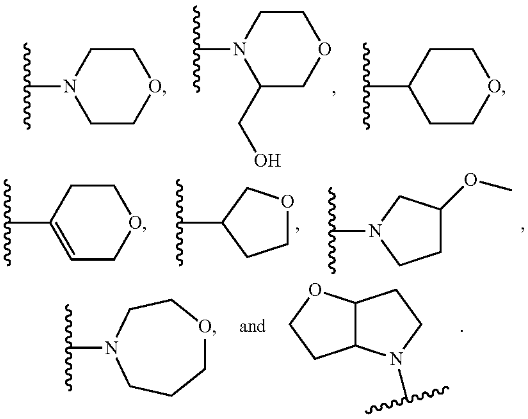

3. The compound of claim 1, wherein ring A is 5-membered heteroaryl having at least one nitrogen ring atom.

4. The compound of claim 1, wherein ring A is selected from

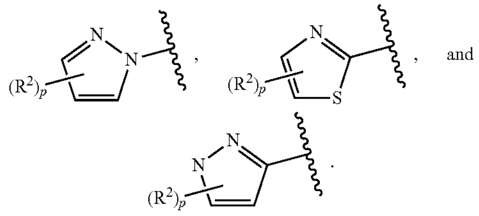

5. The compound of claim 1, wherein ring A is selected from

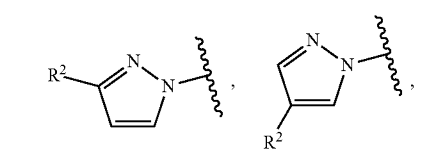

and

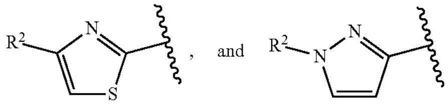

6. The compound of claim 1, wherein $L^1$ is absent.

7. The compound of claim 1, wherein $L^2$ is $—OCH_2CH_2—$, $—OCH_2—$, or $—OCH_2CH_2CH(OH)CH_2—$.

8. The compound of claim 1, wherein the moiety

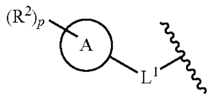

is selected from,

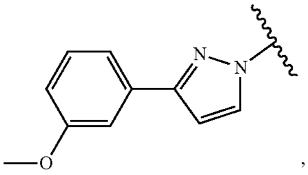

,

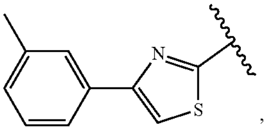

,

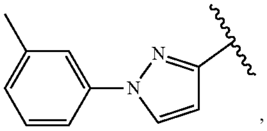

,

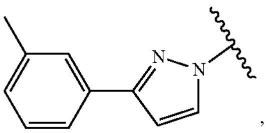

,

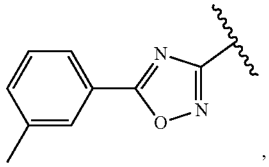

,

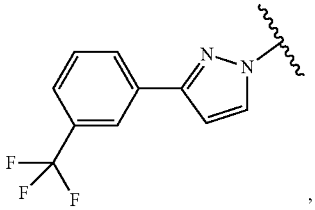

,

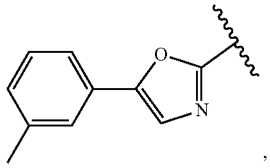

,

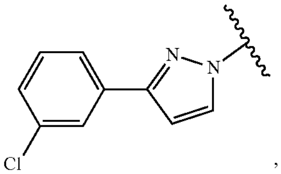

,

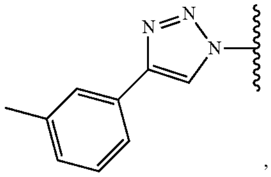

, and

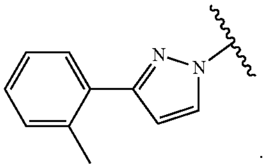

.

9. A compound of the formula (II)

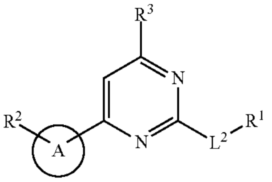

(II)

or a pharmaceutically acceptable salt thereof, wherein $R^1$ is hydroxy, substituted or unsubstituted heteroaryl, or substituted or unsubstituted heterocyclyl;

$R^2$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted heterocyclyl;

$R^3$ is substituted or unsubstituted oxygen-containing heterocyclyl;

Ring A is 5-membered heteroaryl having at least one nitrogen ring atom;

$L^2$ is $—O—(CR^aR^b)_m—$;

each occurrence of $R^a$ and $R^b$ are independently hydrogen, hydroxy, or hydroxy$(C_{1-4})$alkyl; and m is 1-4.

10. The compound of claim 9, wherein $R^3$ is selected from

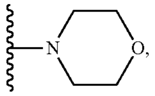

,

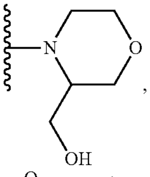

,

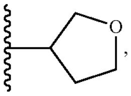

, and

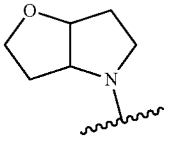

.

11. The compound of claim 10, wherein $R^3$ is

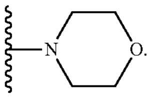

.

12. The compound of claim 9, wherein ring A is selected from

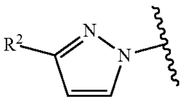

,

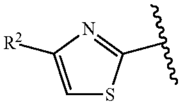

, and

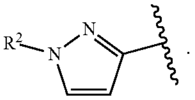

.

13. A compound selected from
1
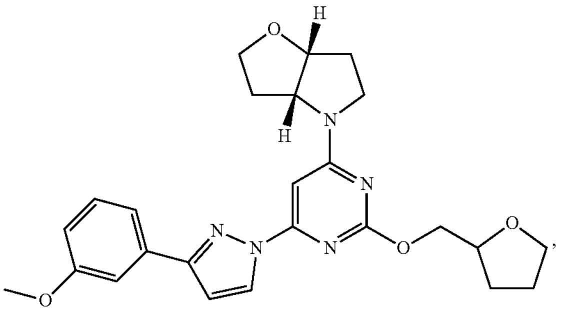
2
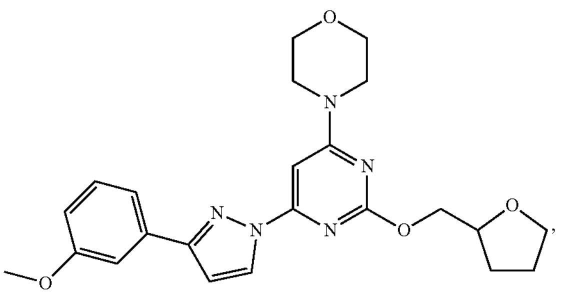
3
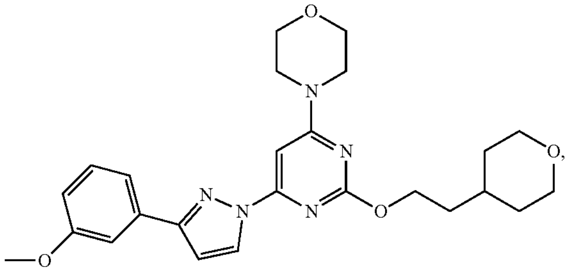
4
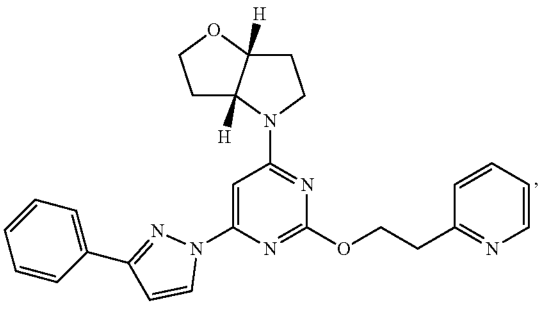
5
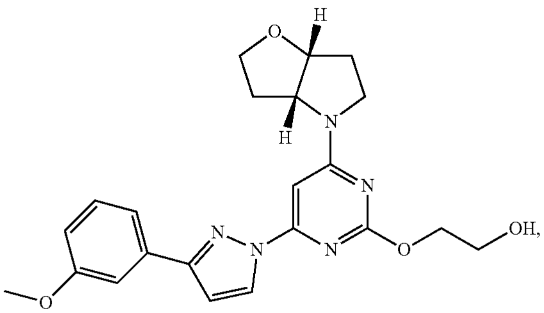
-continued
6
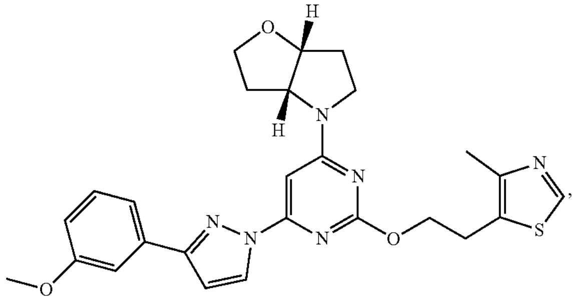
7
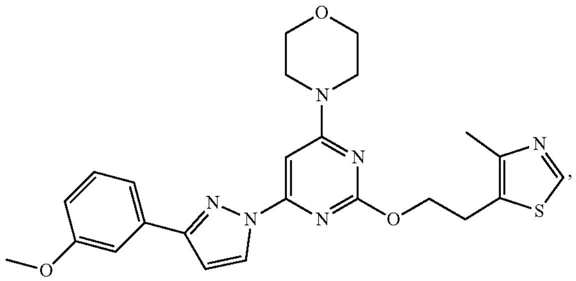
8
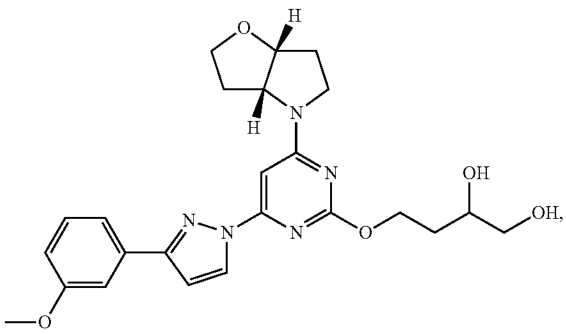
9
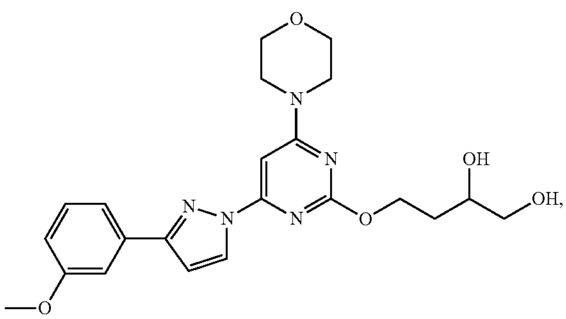

-continued
10
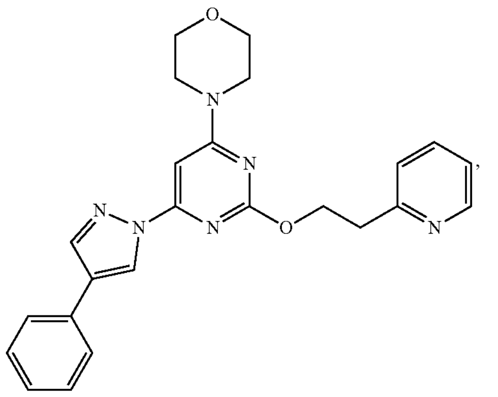
11
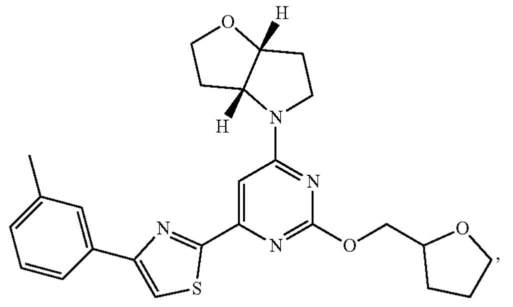
12
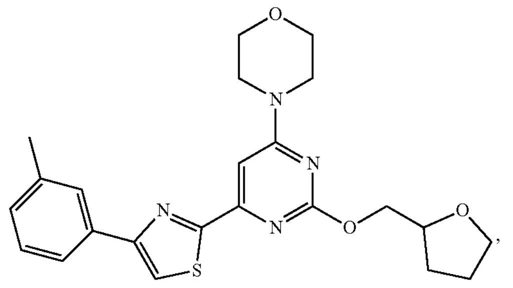
13
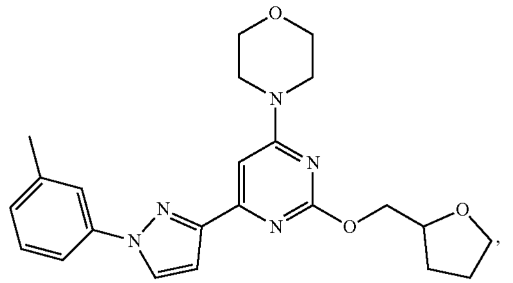
14
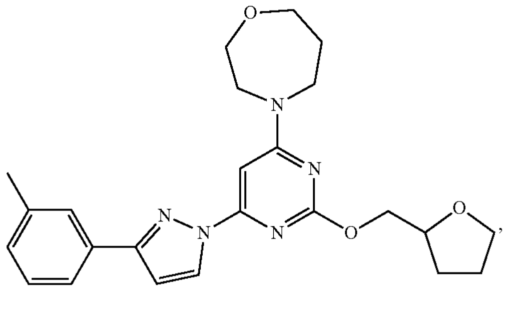
-continued
15
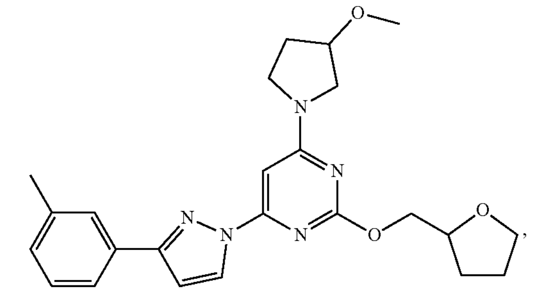
16
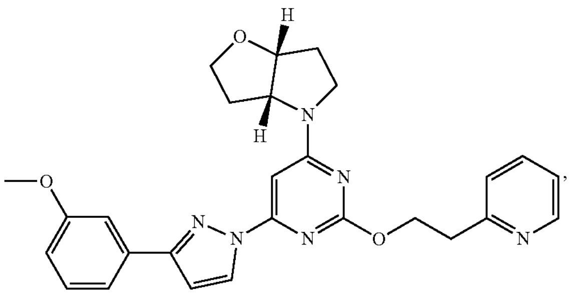
17
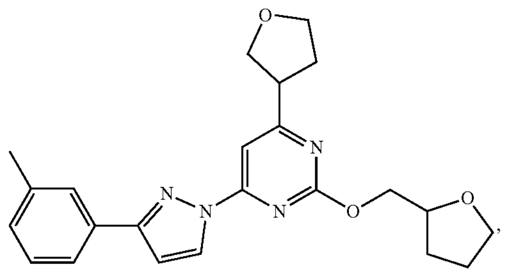
18
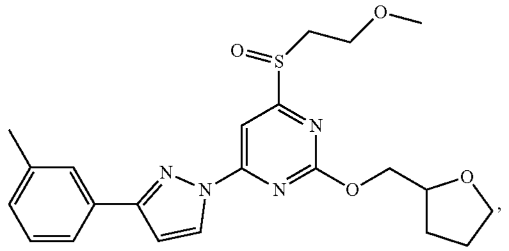
19
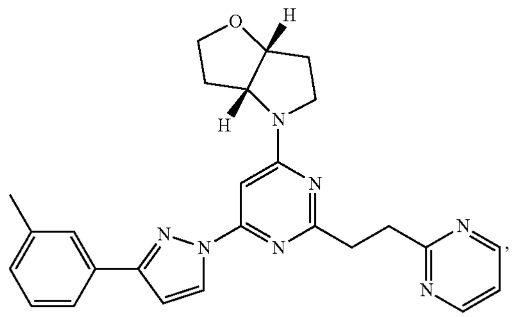

-continued

20

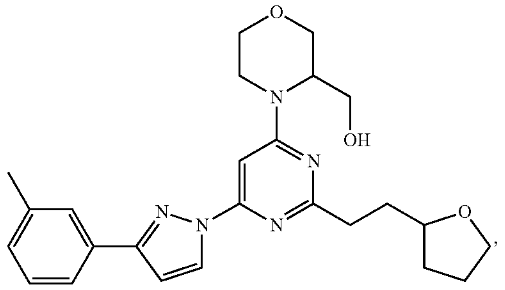

and pharmaceutically acceptable salts thereof.

14. The compound of claim 13, wherein the compound is selected from

2

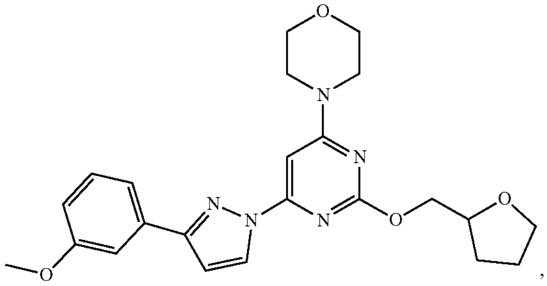

,

3

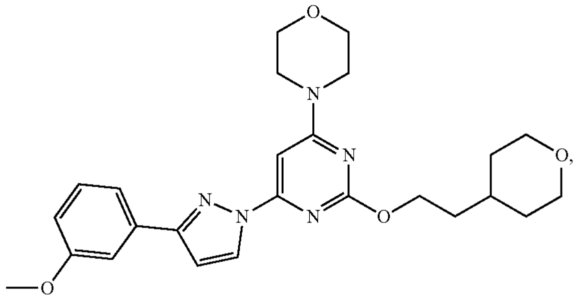

7

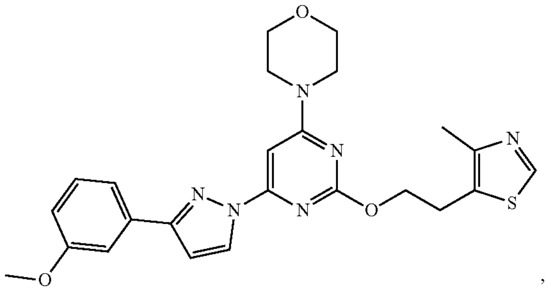

,

-continued

9

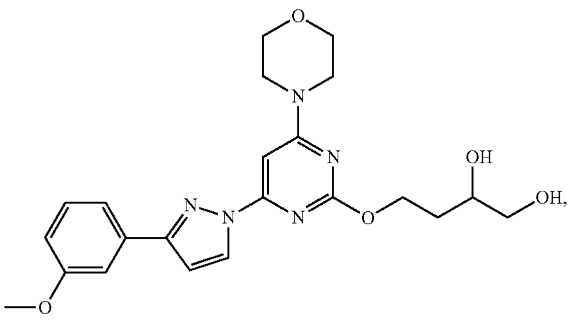

and pharmaceutically acceptable salts thereof.

15. The compound of claim 14, wherein the compound is

2

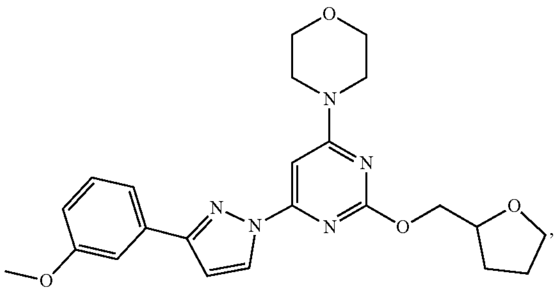

and pharmaceutically acceptable salts thereof.

16. The compound of claim 14, wherein the compound is

3

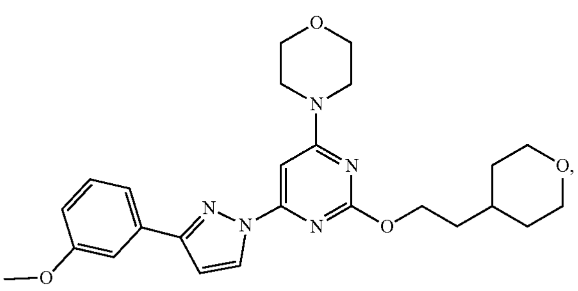

and pharmaceutically acceptable salts thereof.

17. The compound of claim 14, wherein the compound is
7
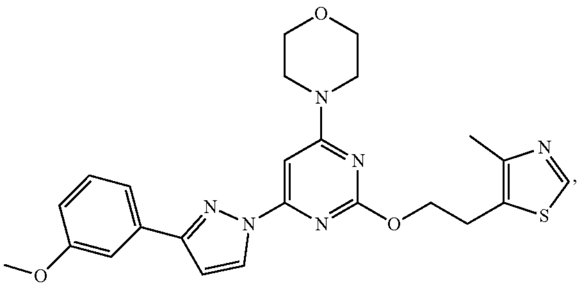,
and pharmaceutically acceptable salts thereof.
18. The compound of claim 14, wherein the compound is
9
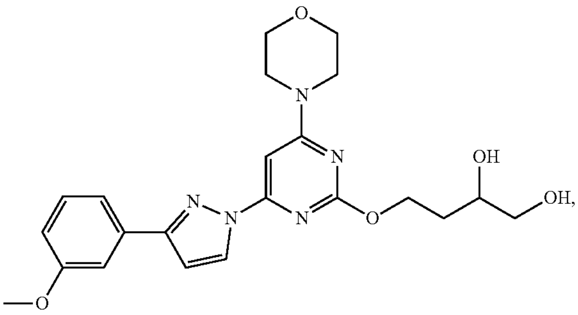,
and pharmaceutically acceptable salts thereof.
* * * * *